(12) United States Patent
Peters

(10) Patent No.: US 6,858,017 B2
(45) Date of Patent: Feb. 22, 2005

(54) ANKLE BRACE WITH CUFF AND STRAP

(75) Inventor: Rick E. Peters, Indianapolis, IN (US)

(73) Assignee: Ultra Athlete LLC, Indianapolis, IN (US)

( * ) Notice: Subject to any disclaimer, the term of this patent is extended or adjusted under 35 U.S.C. 154(b) by 0 days.

(21) Appl. No.: 10/783,902

(22) Filed: Feb. 20, 2004

(65) Prior Publication Data

US 2004/0167453 A1 Aug. 26, 2004

Related U.S. Application Data

(62) Division of application No. 09/925,335, filed on Aug. 9, 2001, now Pat. No. 6,749,578, which is a continuation-in-part of application No. PCT/US00/03385, filed on Feb. 9, 2000, which is a continuation of application No. 09/252,582, filed on Feb. 18, 1999, now Pat. No. 6,053,884.
(60) Provisional application No. 60/283,893, filed on Apr. 13, 2001.

(51) Int. Cl.$^7$ ................................................. A61F 5/00
(52) U.S. Cl. ............................ 602/27; 602/5; 602/16; 602/23
(58) Field of Search .............................. 602/5, 16, 27, 602/23; 2/22; 482/79; 36/88, 89, 115, 116, 117.1

(56) References Cited

U.S. PATENT DOCUMENTS

| 76,353 | A | 4/1868 | Sherer |
|---|---|---|---|
| 1,205,206 | A | 11/1916 | Hofmeister |
| 2,444,428 | A | 7/1948 | Carrier |
| 2,973,757 | A | 3/1961 | Katthoefer |
| 3,086,521 | A | 4/1963 | Desai et al. |
| 3,405,463 | A | 10/1968 | Werner |
| 4,280,489 | A | 7/1981 | Johnson, Jr. |
| 4,517,968 | A | 5/1985 | Greene et al. |
| 4,565,017 | A | 1/1986 | Ottieri |
| 4,587,962 | A | 5/1986 | Greene et al. |
| 4,665,904 | A | 5/1987 | Lerman |
| 4,693,239 | A | 9/1987 | Clover, Jr. |
| 4,834,078 | A | 5/1989 | Biedermann |
| RE33,395 | E | 10/1990 | Peters |
| 5,031,607 | A | 7/1991 | Peters |
| 5,056,509 | A | 10/1991 | Swearington |
| 5,069,202 | A | 12/1991 | Prock |
| 5,090,138 | A | 2/1992 | Borden |
| 5,175,947 | A | 1/1993 | Parracho |
| 5,177,884 | A | 1/1993 | Rullier |
| 5,209,722 | A | 5/1993 | Miklaus et al. |
| 5,542,912 | A | 8/1996 | Hess |
| 5,678,330 | A | 10/1997 | Van Dyke et al. |
| D391,640 | S | 3/1998 | Oviedo, Jr. |
| 5,778,563 | A | 7/1998 | Ahlbaumer |
| 5,891,072 | A | 4/1999 | Cady, Jr. |
| 6,053,884 | A | 4/2000 | Peters |
| 6,350,246 | B1 | 2/2002 | De Toro et al. |
| 6,524,266 | B1 | 2/2003 | Peters |
| 2001/0056251 | A1 | 12/2001 | Peters |

FOREIGN PATENT DOCUMENTS

| DE | 4404911 A1 | 8/1995 |
|---|---|---|
| EP | 0416913 A3 | 3/1991 |
| IT | 562222 | 5/1957 |

*Primary Examiner*—Kim M. Lewis
(74) *Attorney, Agent, or Firm*—Camoriano and Associates; Theresa Fritz Camoriano

(57) ABSTRACT

An ankle brace includes a heel stirrup including a base and left and right upright portions. Left and right pivot legs are pivotably connected to the left and right uprights, respectively. A cuff joins the left and right pivot legs. In most preferred embodiments, the rear cuff is flexible.

4 Claims, 25 Drawing Sheets

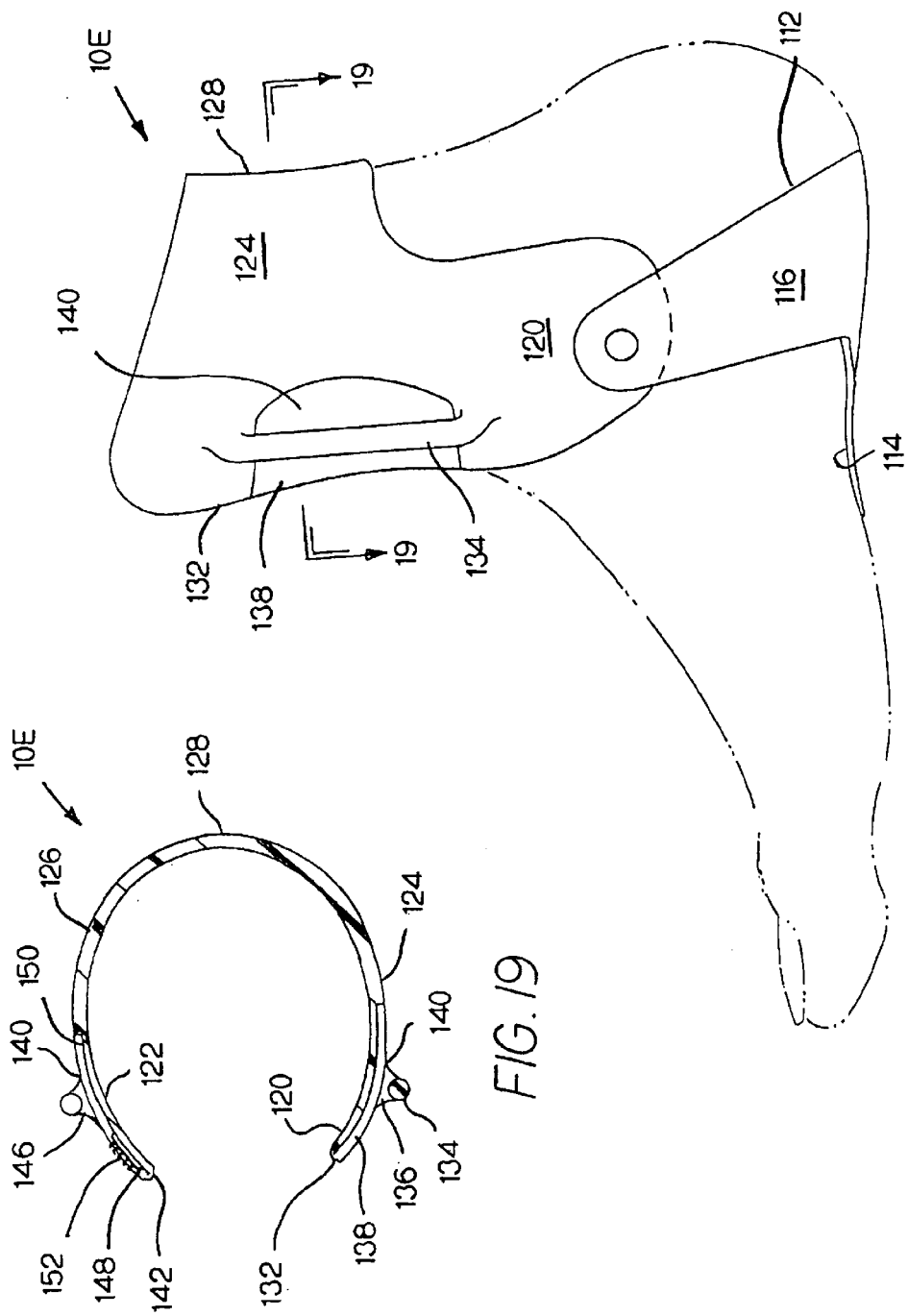

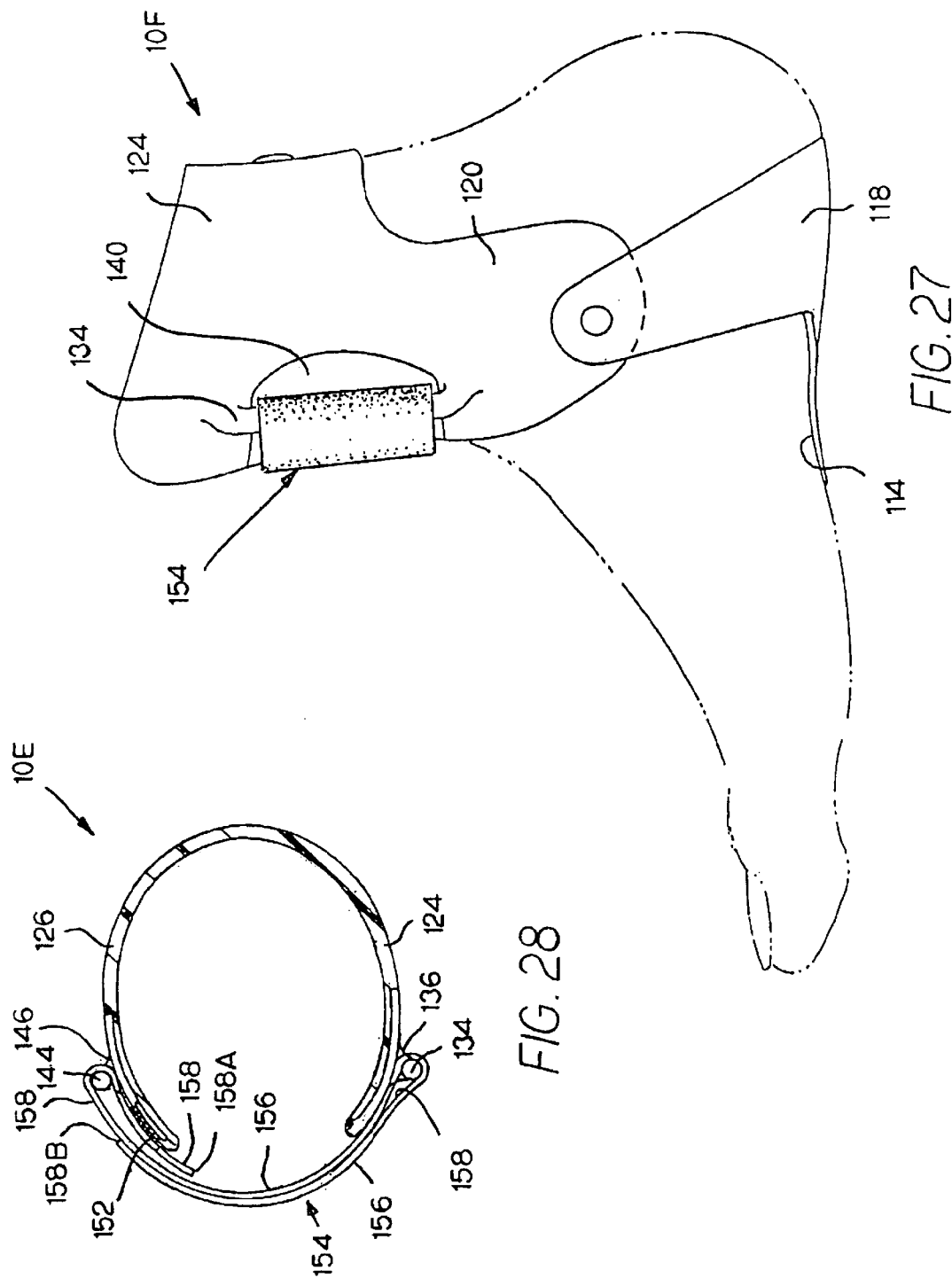

ANKLE BRACE WITH CUFF AND STRAP

This application is a divisional of U.S. patent application Ser. No. 09/925,335, filed Aug. 9, 2001, now U.S. Pat. No. 6,749,578, which is a continuation-in-part of and claims priority from Patent Application PCT/US00/03385 filed Feb. 9, 2000, which is a continuation of U.S. patent application Ser. No. 09/252,582, now U.S. Pat. No. 6,053,884, filed Feb. 18, 1999, (Priority date of 18 Feb. 1999) and it claims priority from U. S. Provisional Patent Application Ser. No. 60/283,893 (Ankle Brace with Strap Attachment), filed Apr. 13, 2001.

BACKGROUND OF THE INVENTION

The present invention relates to ankle braces, and, in particular, to an ankle brace that provides greater comfort and support than braces of the prior art.

Many types of ankle braces are known, including my earlier design, described in U.S. Pat. No. Re. 33,395. That brace provided greater flexibility and comfort than other braces, because it provided pivots on both sides of the brace, which enabled the foot to flex forward and backward while limiting side-to-side motion of the foot relative to the leg in order to protect the injured ankle. That brace had left and right pivot legs, which were intended to lie along the left and right sides of the wearer's leg, and there were straps which wrapped around the leg to hold the pivot legs together. While the straps provide flexibility of movement, they also stretch and shift, thereby sacrificing some structural support.

Also, in prior art designs, the semi-rigid stirrup encircled the bottom of the foot, interfering with a person's foot spreading out as he put his weight on the foot, thereby causing irritation and pain. If the stirrup were made wide enough to avoid that problem, it would provide less support to the person's ankle and might be too wide to fit into the person's shoe.

SUMMARY OF THE INVENTION

The present invention provides the desired front-to-back flexibility of the prior art braces, and, in addition, provides improved structure so that there is additional structural support preventing side-to-side movement of the ankle.

In particular, most of the preferred embodiments of the present invention provide arms, extending from the left and right pivot legs, which are joined together to form a flexible rear cuff. The phrase "flexible rear cuff" means a rear cuff that provides greater flexibility than would be provided by joining the arms together to form the cuff as a unitary piece having substantially the same thickness, continuity, and height as the arms themselves The flexibility may be achieved by cutting out portions of the unitary rear cuff to make it substantially more flexible, or by changing the dimensions of a portion of the unitary rear cuff so that it is substantially thinner or shorter than the arms, or both, thereby creating a substantially more flexible section. Also, if the arms are not formed as a unitary piece, the mechanical arrangement by which the arms are joined together to form the cuff may provide the flexibility. For example, in one preferred embodiment, the arms are connected together by a rivet which permits them to pivot relative to each other. This pivot connection allows the brace to be adjusted in order to fit a wide variety of people's foot and leg shapes, resulting in a comfortable brace, while providing more support than prior art designs. The arms, pivoted together, limit the range of motion between the pivot legs while providing the desired flexibility so that the wearer can continue to flex and exercise the ankle while the ankle is protected and supported by the brace. Most of the other embodiments use other mechanisms for providing a controlled, flexible connection between the arms.

The preferred embodiments of the present invention also provide a heel stirrup and a tongue, extending forward of the heel stirrup. The heel stirrup surrounds the heel to provide the greatest possible stability while leaving the bottom of the foot, including the arch, free to spread out, so that the stirrup does not impinge on the wearer's foot.

The preferred embodiments of the present invention also provide an ankle brace with a single strap closure mechanism that provides the wearer easy enhanced structural support, adjustability for ankle size, and ease of use.

BRIEF DESCRIPTION OF THE DRAWINGS

FIG. 18 is a side view of the ankle brace of FIG. 17;

FIG. 19 is a view along the line 19—19 of FIG. 18;

FIG. 27 is a side view of the ankle brace of FIG. 22, with the strap shown securing the ankle brace to the wearer's leg;

FIG. 28 is a the same view as FIG. 19, but with the strap in place as in FIG. 27;

DESCRIPTION OF THE PREFERRED EMBODIMENTS

Figure 1:
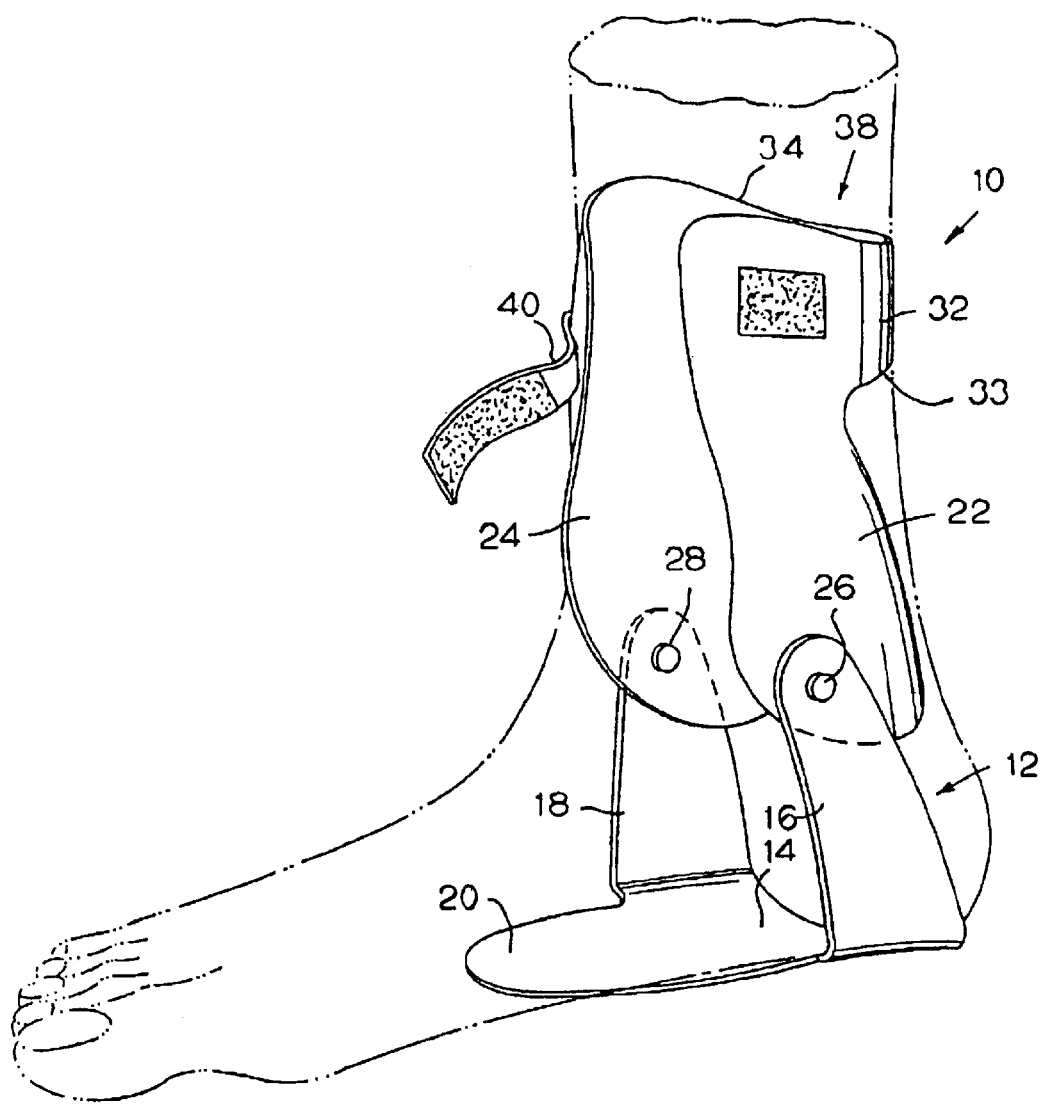
FIG. 1 is a perspective view of an ankle brace made in accordance with the present invention, with a wearer's foot shown in phantom.

FIGS. 1–5 show an ankle brace 10, which is made up of three main pieces. The first piece is the heel stirrup 12, which is substantially U-shaped, and includes a base or bottom portion 14 and left and right upright portions 16, 18. The upright portions 16, 18 project upwardly and forwardly from the rear of the base portion 14, which permits them to wrap around the heel, which provides for the greatest support, while still locating the pivots 26, 28 adjacent to the ankle, to provide the greatest comfort and flexibility. The horizontal distance "A" from the axis of the pivots 26, 28 to the rear of the stirrup 12 preferably is at least one inch. The horizontal distance "B" from the rear edge of the upright portion 16 at the height of the pivot 26 to the rear edge of the base 14 preferably is at least 0.75 inches. This location of the upright portions 16, 18 also prevents the stirrup 12 from interfering with the spreading of the foot. A tongue 20 extends forward from the forward edge 14A of the bottom portion 14 of the stirrup 12 to provide additional support, again without interfering with the foot. The entire stirrup 12, including bottom portion 14, upright portions 16, 18, and tongue 20 are preferably molded or otherwise formed from a single piece of material. It would, of course, be possible to use separate pieces of material and connect them together to form the stirrup 12, but a single piece is preferable.

Figure 2:
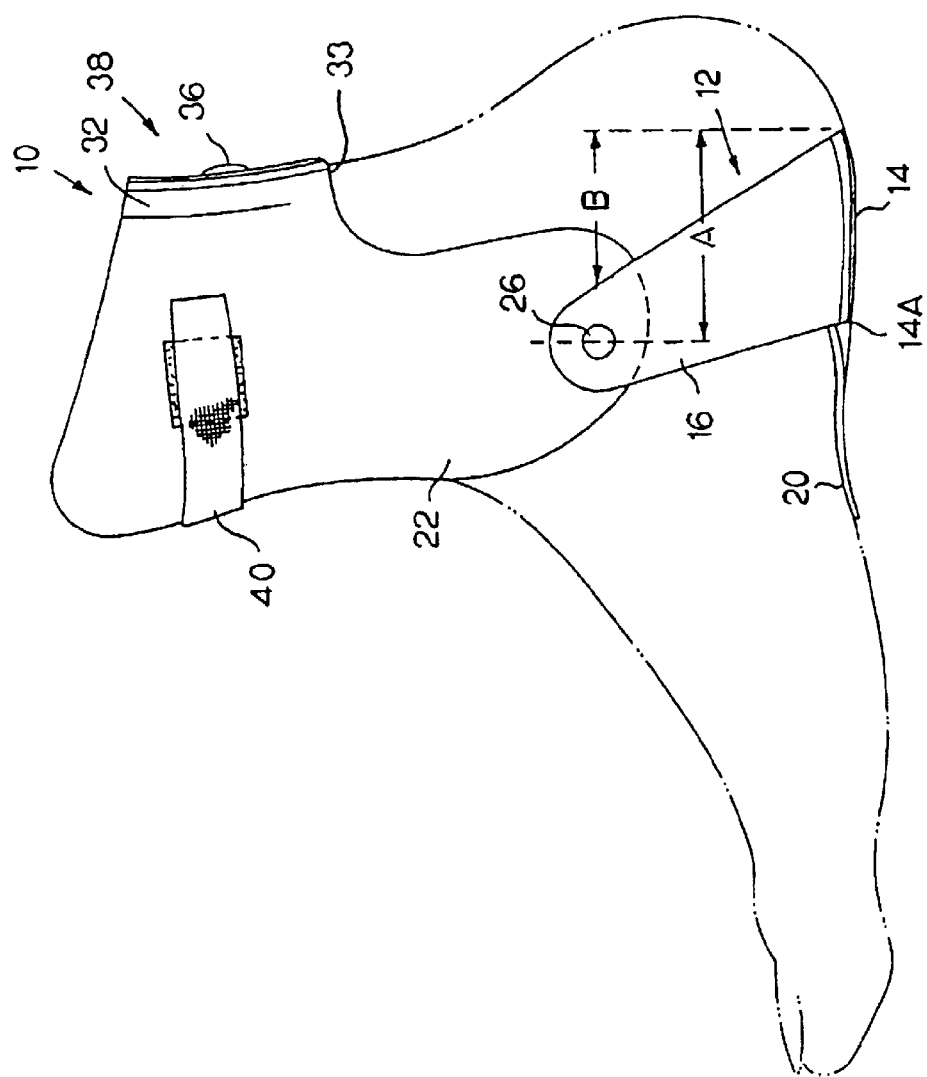
FIG. 2 is a side view of the ankle brace of FIG. 1.
Figure 3:
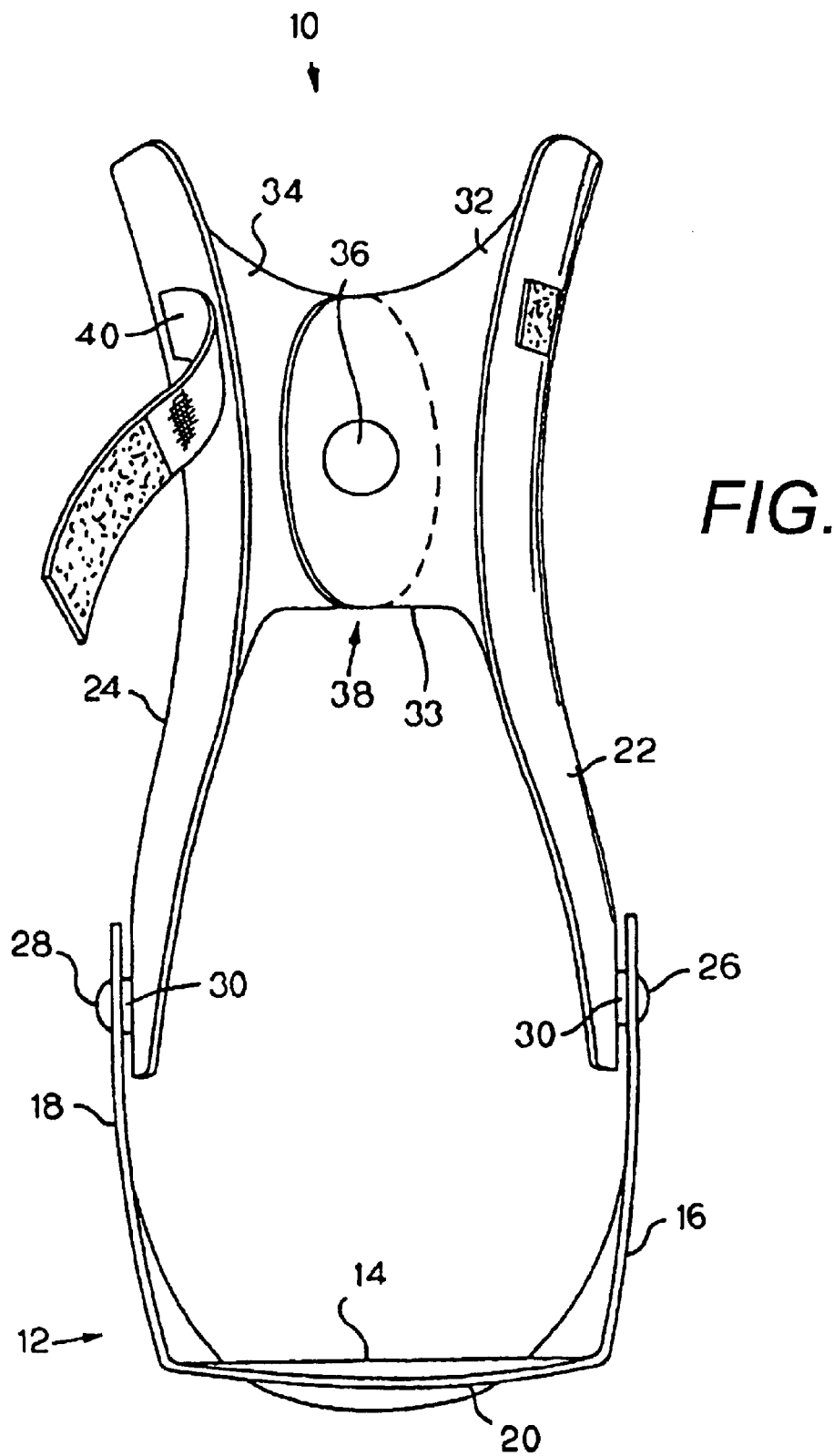
FIG. 3 is a front view of the ankle brace of FIG. 1.
Figure 4:
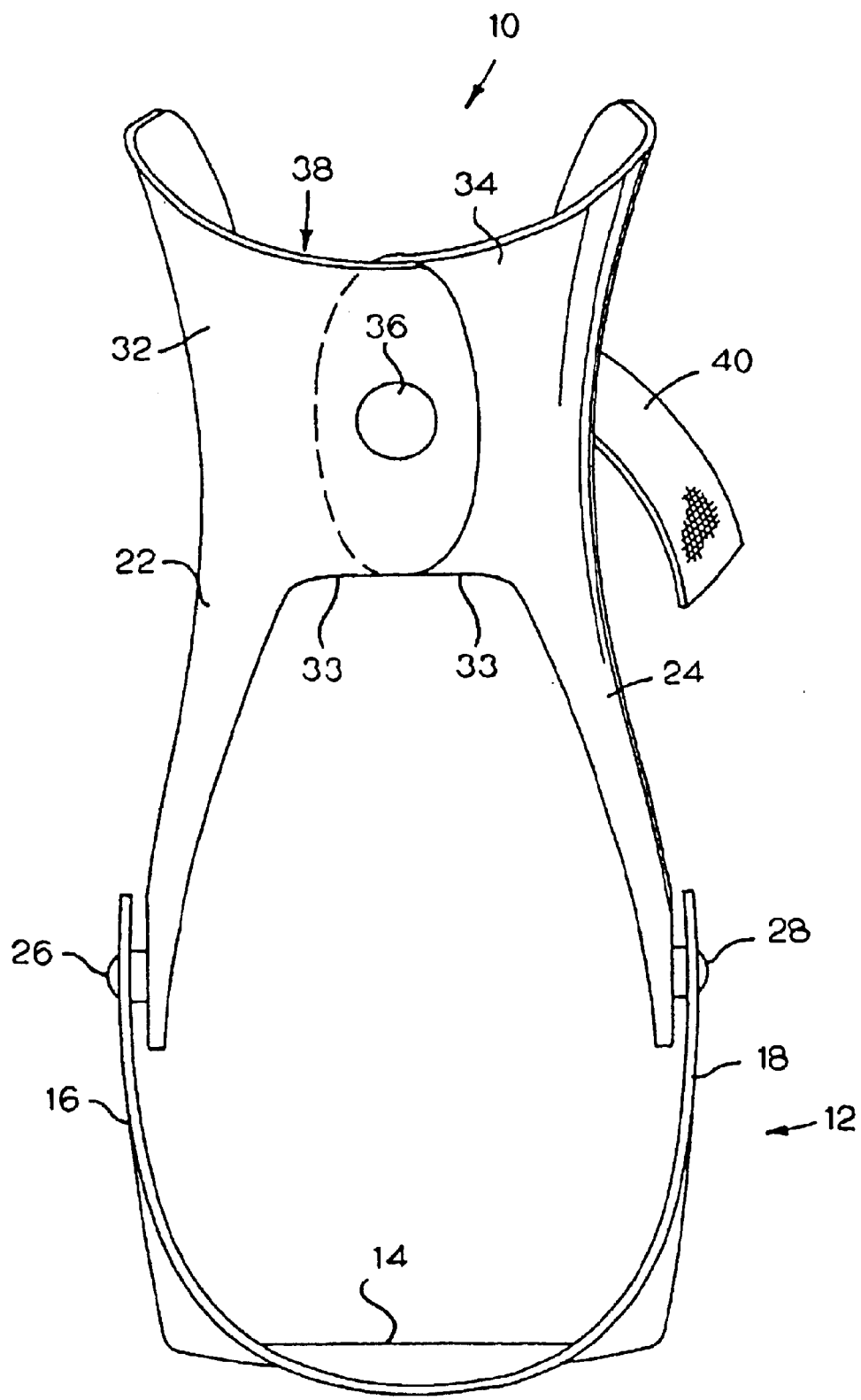
FIG. 4 is a rear view of the ankle brace of FIG. 1.
Figure 5:
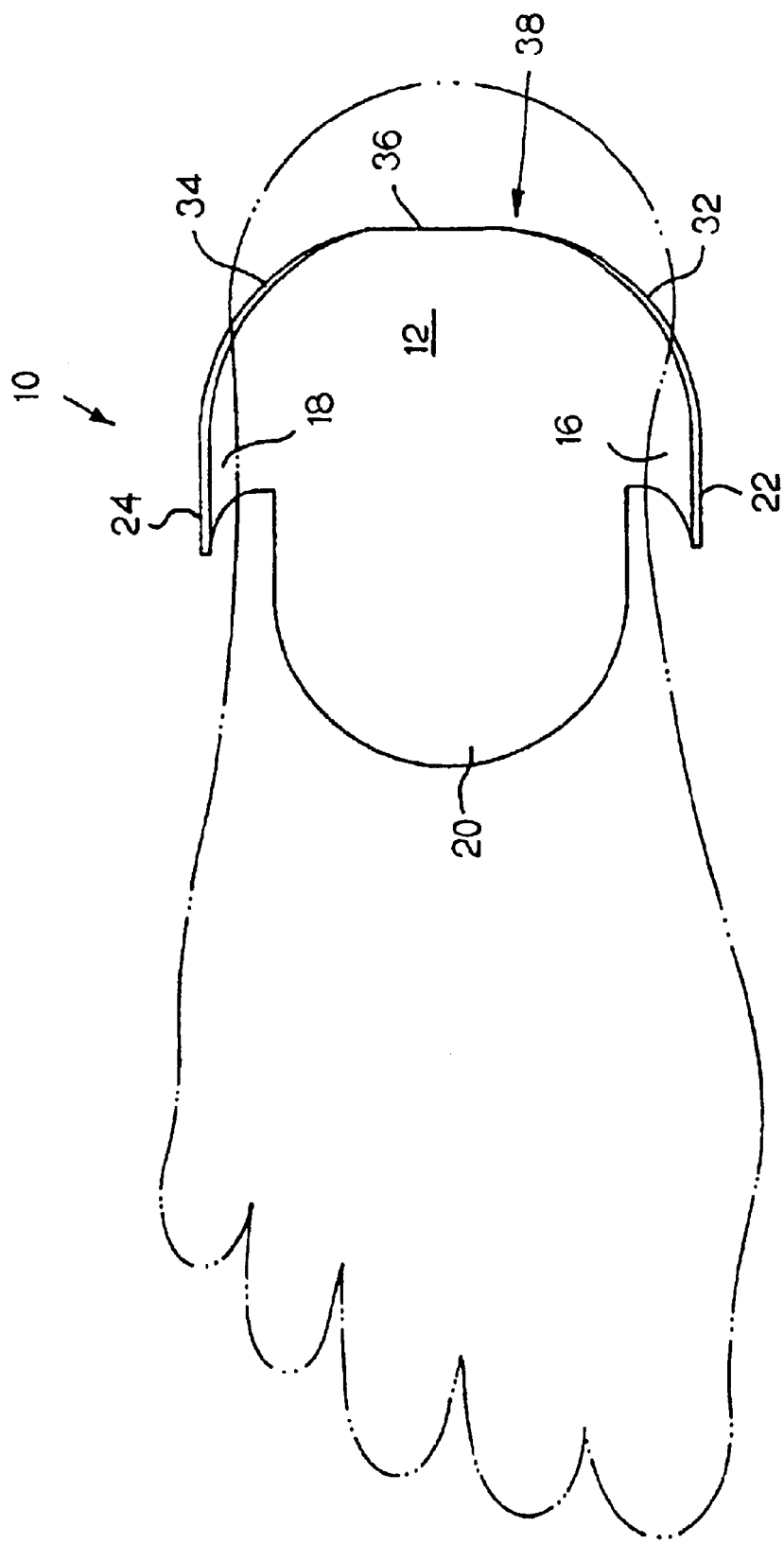
FIG. 5 is a top view of the ankle brace of FIG. 1.

The second and third pieces are the left and right pivot legs 22, 24, which are pivotably connected to the left and right uprights, 16, 18, respectively, at the left and right pivot points 26, 28. The pivots 26, 28 are formed from bolts, rivets, or other connectors extending through the respective uprights and pivot legs, as shown best in FIG. 3 and are located approximately at the location of a wearer's ankle, so that the brace pivots forward and backward with the person's ankle. The two ankle pivot points 26, 28 preferably are at the same height. As shown in FIG. 2, the axis of the pivots 26, 28 is directly above the forward edge 14A of the bottom portion 14 of the stirrup 12. Also, as shown in FIG. 3, there preferably are spacers or washers 30 between the connected uprights and pivot legs to prevent them from rubbing against each other as they pivot.

The left and right pivot legs 22, 24 have rearwardly-projecting arms 32, 34, which overlap each other and are fastened together with a bolt, rivet, pin, or other connector to form a rear pivot point 36. The rear pivot point 36 is located along an imaginary vertical plane bisecting the brace 10, and its axis of rotation is substantially orthogonal to an imaginary vertical plane extending through the two ankle pivots 26, 28. A rear cuff 38 is formed by the two rearwardly-projecting arms 32, 34. The left pivot leg 22 and left arm 32 preferably are formed of a single piece of material, and, even if they are formed of separate pieces, it is preferred that the arm 32 be made of material at least as rigid as the leg 22 to which it is attached. This is also preferred with respect to the right pivot leg 24 and right arm 34.

A strap 40 is fastened at one end to the right pivot leg 24 and includes a strip of hook-and-loop fastener on its free end, and there is a mating piece of hook-and-loop fastener fixed to the left pivot leg 22, so that a wearer can put the brace on and then wrap the strap 40 around the front of his leg and fasten it to the left pivot leg 22 to hold the brace 10 on.

The brace 10 is shown here being used on the wearer's right foot, but the identical brace 10 could also be used on the left foot, as the brace is essentially symmetrical about a central vertical plane.

Figure 7:
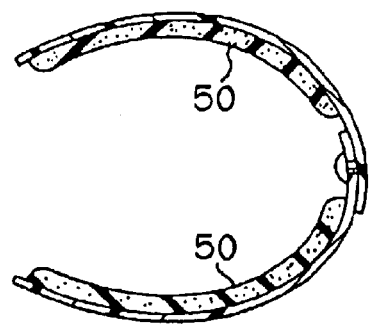
FIG. 7 is a view taken along the section 7—7 of FIG. 6.
Figure 6:
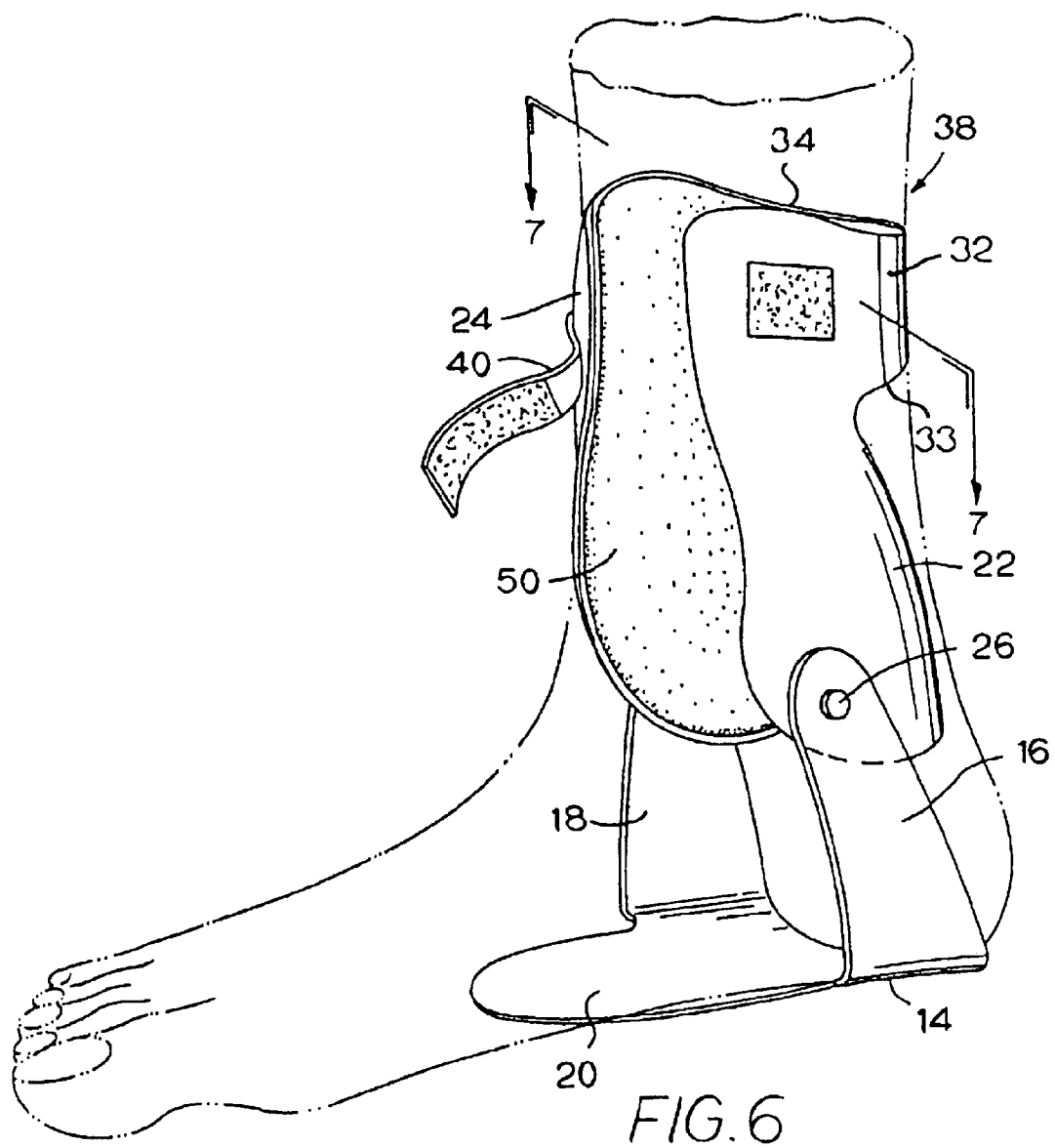
FIG. 6 is the same view as FIG. 1, but with padding added to the interior of the brace.

FIGS. 6 and 7 show the brace 10 of FIGS. 1–5 modified by the addition of padding 50 on the interior surface of the legs 22, 24 and arms 32, 34 of the brace. While these drawings show the use of foam padding, many different types of pads, including air pillows, gel packs, and so forth, may be used.

Figure 8:
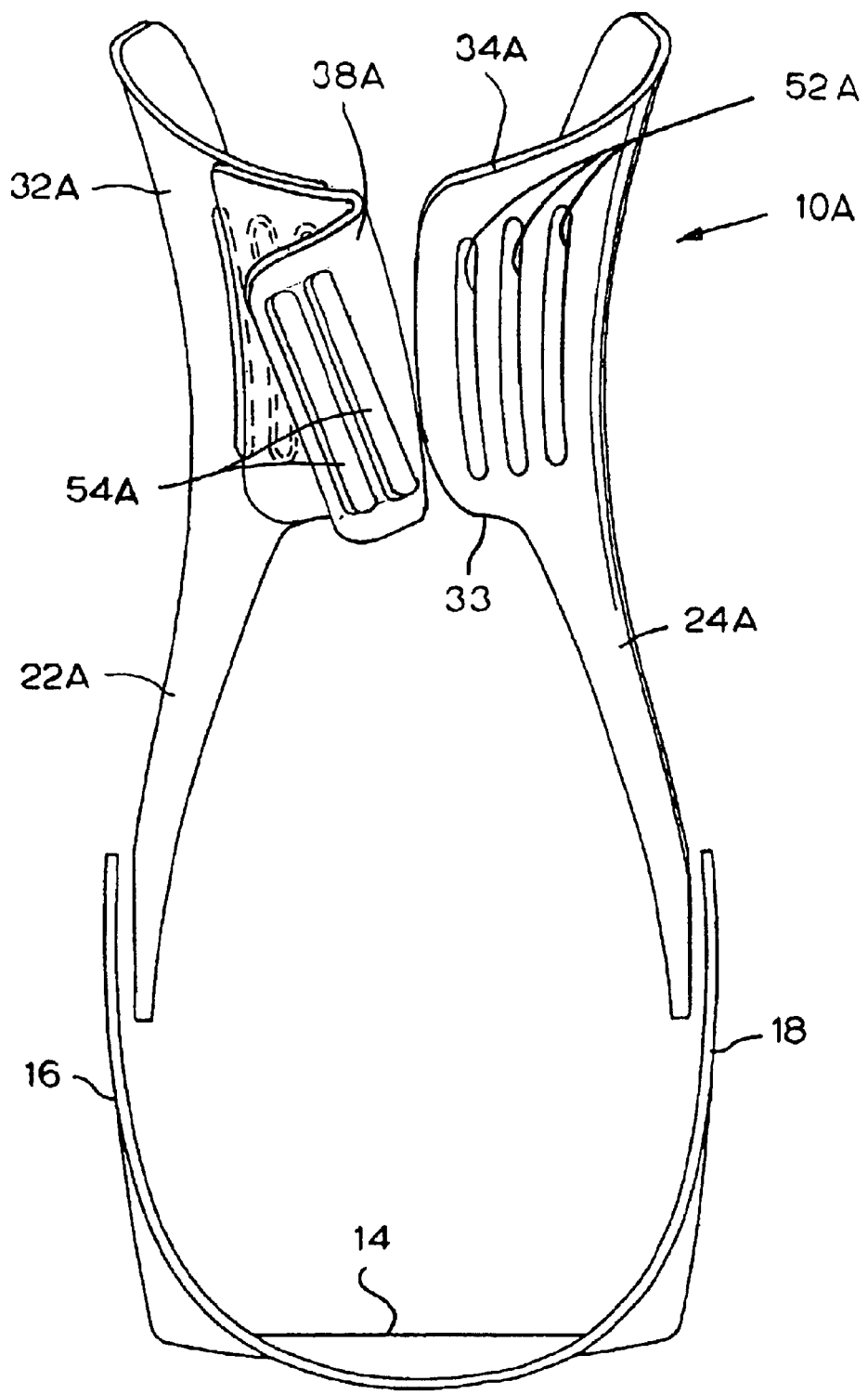
FIG. 8 is a rear view of a second embodiment of an ankle brace made in accordance with the present invention, with a separate, slotted rear cuff (peeled back to depict how it attaches) which provides flexibility and adjustability.
Figure 9:
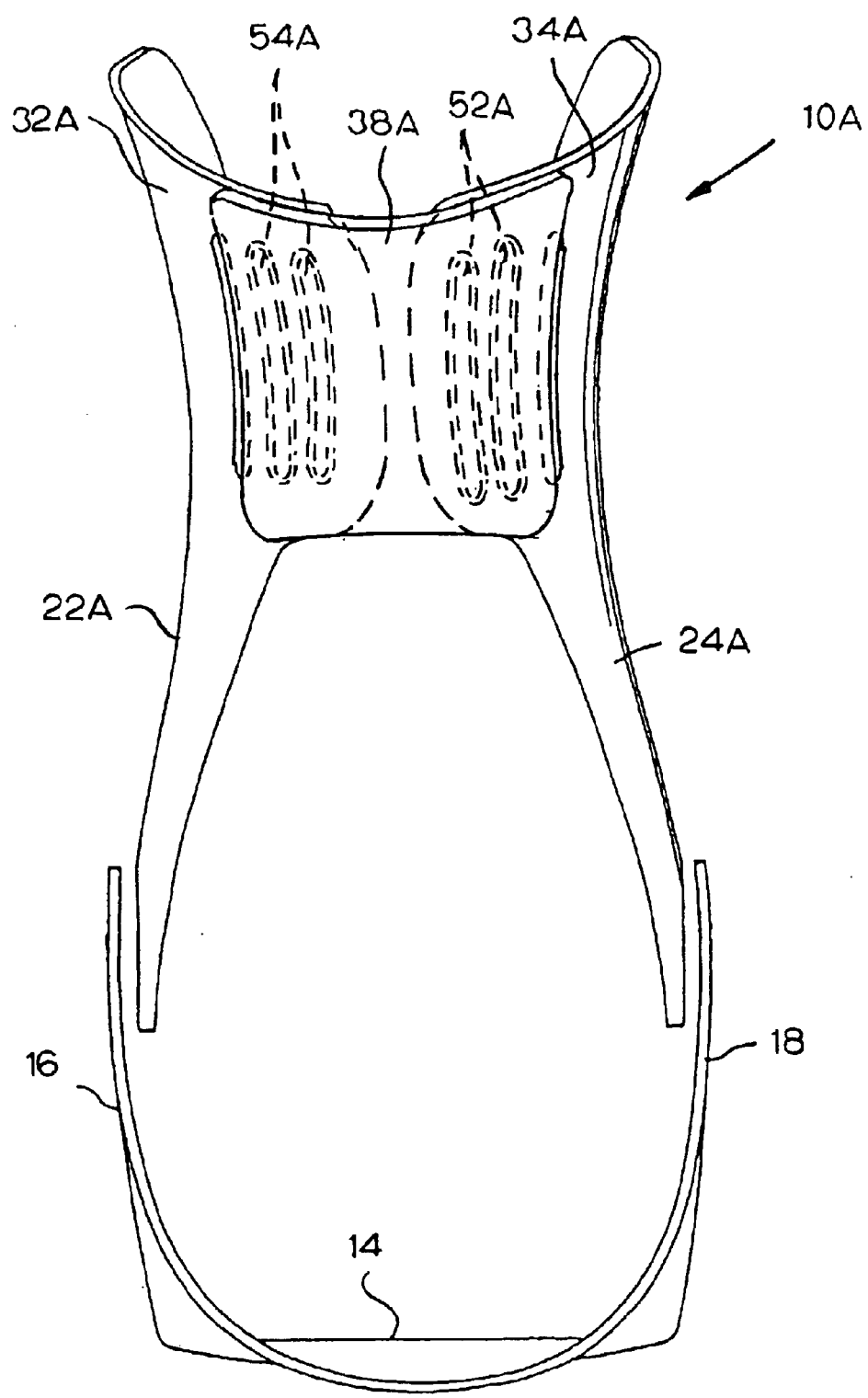
FIG. 9 is the same view as in FIG. 8 but with the rear cuff attached at both ends.

FIGS. 8 and 9 show another embodiment of a brace 10A, in which the left and right rearwardly projecting arms 32A, 34A do not quite overlap each other. Each of the arms 32A, 34A has a plurality of slightly curved, substantially vertically-oriented slotted openings 52A. A separate rear cuff member 38A, which preferably is made of a material that is more flexible than the material of the arms 32A, 34A, has a plurality of mating, substantially-vertically-oriented, elongated ridges 54A projecting from its inner surface (See FIG. 10). These ridges 54A are designed to mate with the slotted openings 52A of the left and right rearwardly projecting arms 32A, 34A. By selecting the slotted openings into which the ridges 54A are inserted, the rear cuff 38A provides an adjustable-length bridge between the two pivot legs 22A, 24A. This arrangement also allows some flexibility of lateral movement of the leg when it is braced within the ankle brace 10A, both by movement of the ridges 54A along their respective slotted openings 52A, and by flexing the rear cuff 38A itself. The shorter the length of the ridges 54A relative to the length of the slotted openings 52A, the more lateral movement of the leg is allowed, while still not permitting the horizontal separation between the two pivot legs 22A, 24A to increase significantly, thus maintaining the leg secured within the ankle brace 10A.

Figure 11:
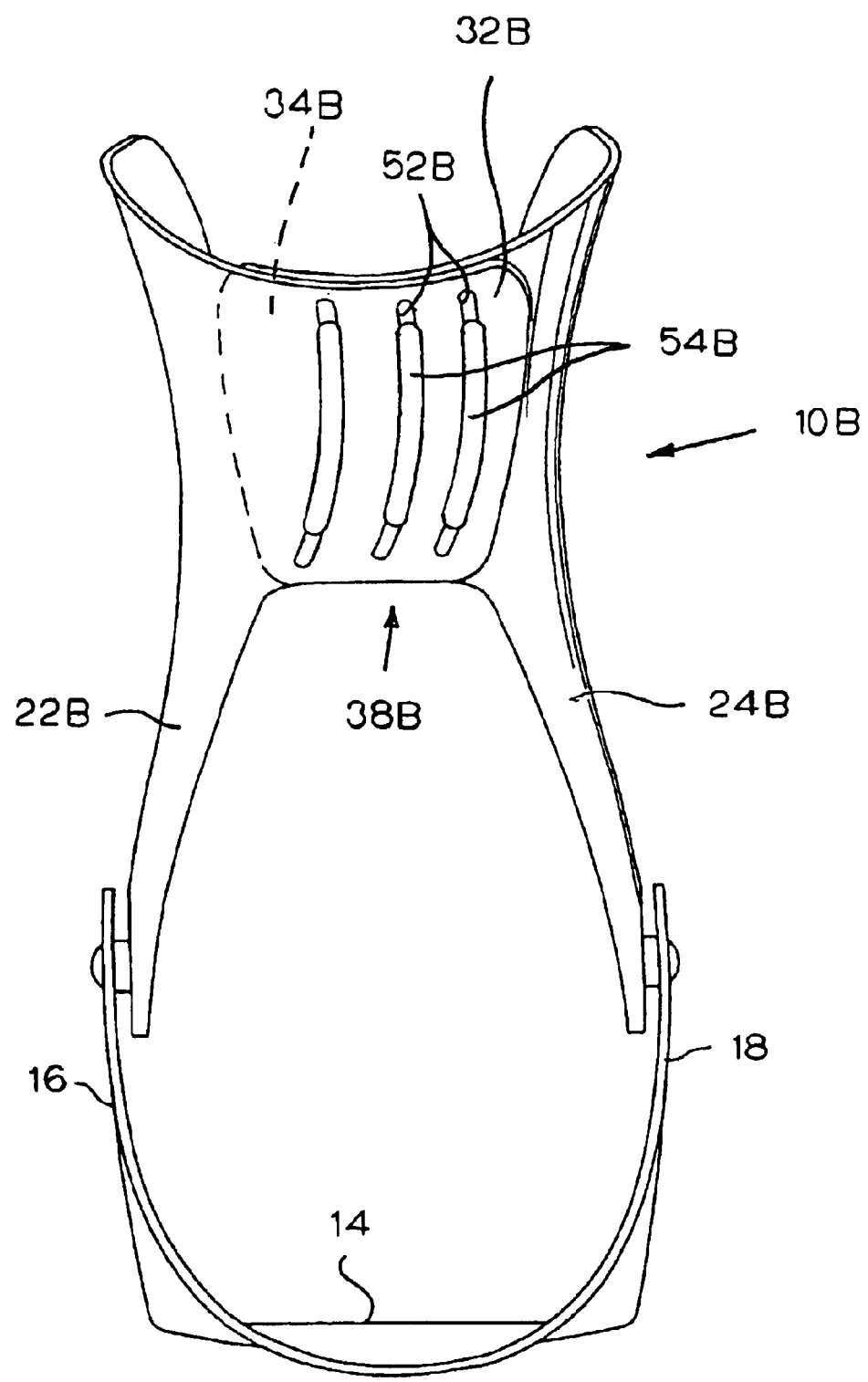
FIG. 11 is a rear view of another embodiment of an ankle brace made in accordance with the present invention, with an integral, slotted rear cuff which provides flexibility and adjustability.
Figure 12:
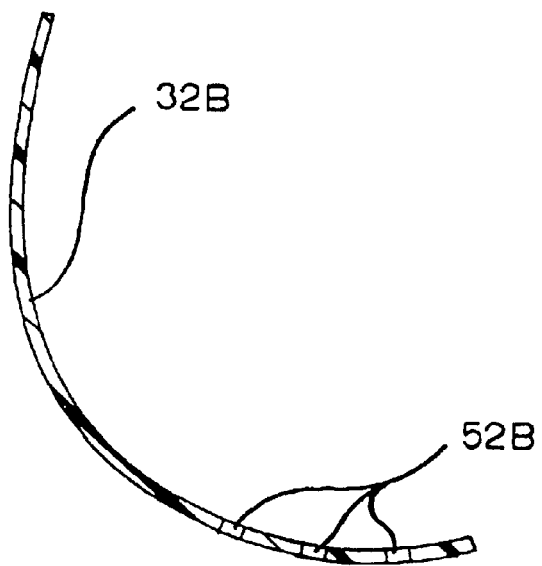
FIG. 12 is a partially broken away top view of the left rear cuff portion of FIG. 11.
Figure 13:
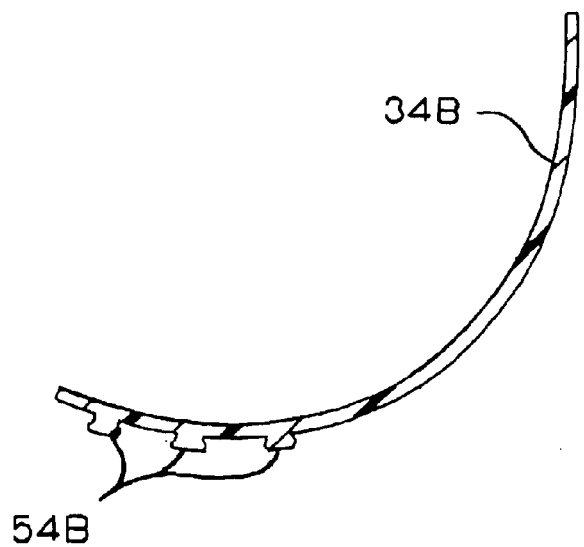
FIG. 13 is a partially broken away top view of the right rear cuff portion of FIG. 11.

FIG. 11 shows yet another embodiment of an ankle brace 10B. In this embodiment, the left and right rearwardly projecting arms 32B, 34B do overlap each other, and one arm 32B has a plurality of substantially-vertically-oriented, arcuate slotted openings 52B, while the second arm 34B has a plurality of substantially-vertically-oriented, elongated ridges 54B projecting from its outer surface (See FIGS. 12 and 13). As in the case of the previous embodiment of the ankle brace 10A, the ridges 54B are designed to mate with the slotted openings 52B such that the rear cuff 38B provides an adjustable-length bridge between the two pivot legs 22B, 24B, and also allows some flexibility of lateral movement of the leg when it is braced within the ankle brace 10B. This ankle brace embodiment 10B works in a very similar manner to that of the previous embodiment 10A; namely, the shorter the length of the ridges 54B relative to the length of the slotted openings 52B, the more lateral movement of the leg is allowed while still not permitting the horizontal separation between the two pivot legs 22B, 24B to increase significantly, thus maintaining the leg secured within the ankle brace 10B. The width of the cuff is adjusted by selecting the slots 52B into which the projections 54B are inserted. As shown in FIG. 11, the cuff is at its narrowest adjustment. To make it wider, only the two outermost projections 54B will be inserted into the two outermost slots 52B, and, to make it wider still, only the one outermost projection 552B will be inserted into the outermost slot 52B. To adjust the amount of flexure that is permitted, the manufacturer adjusts the length of the projections 54B relative to the length of the slots 52B. The greater the difference between the length of the projections and the length of the slots, the greater the amount o flexure that is permitted.

Figure 10:
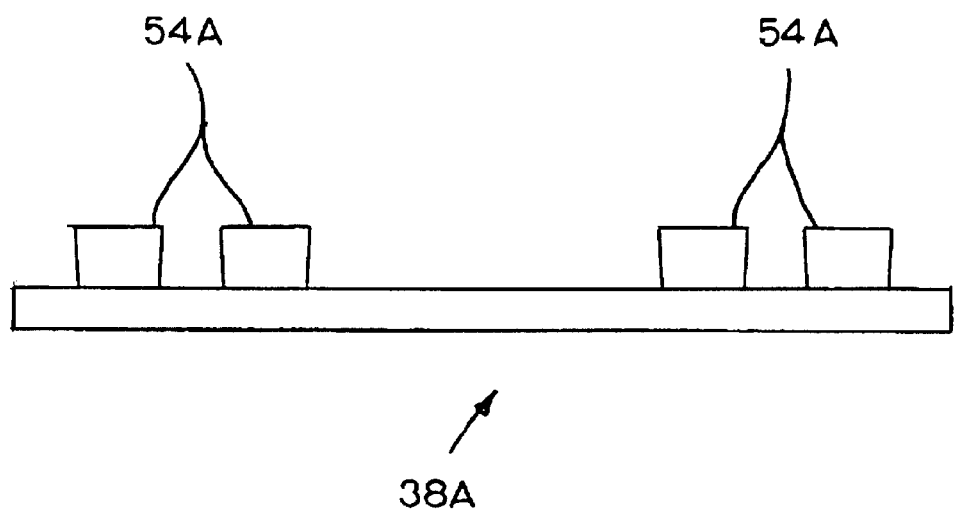
FIG. 10 is a top view of the rear cuff of FIGS. 8 and 9.

It should also be noted in FIG. 10 that the projections have a slight taper along their edges, so they are wider at their outer edge than at the point where they connect to the base, in order to help hold them into the slots. This taper is more pronounced in the embodiment of FIG. 13.

Figure 14:
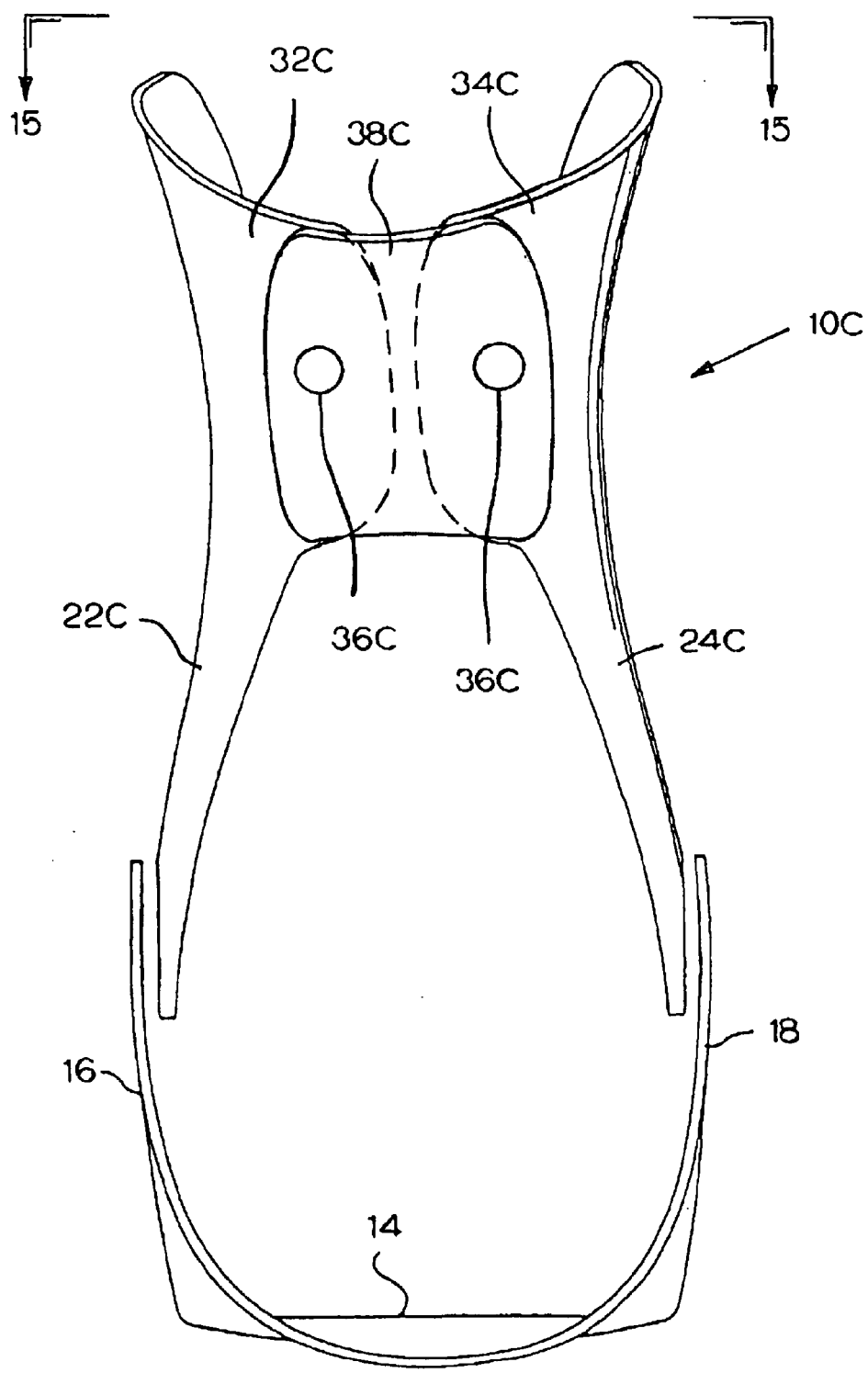
FIG. 14 is a rear view of another embodiment of an ankle brace made in accordance with the present invention, with a separate pivotable rear cuff.
Figure 15:
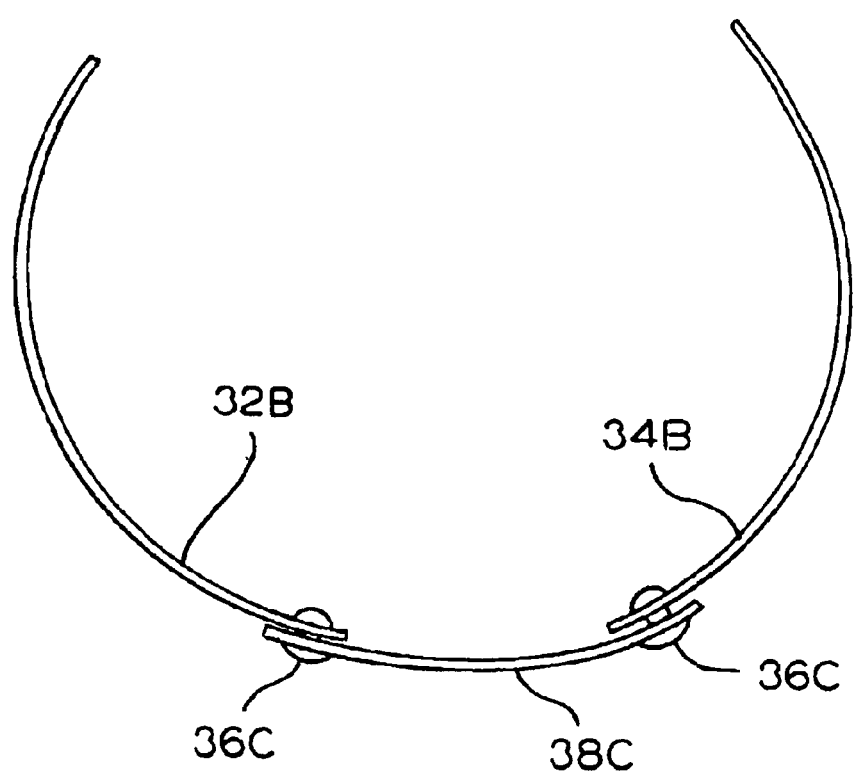
FIG. 15 is a view taken along the line 15—15 of FIG. 14.

FIG. 14 depicts yet another embodiment of an ankle brace 10C, made in accordance with the present invention. In this embodiment, the left and right rearwardly projecting arms 32C, 34C do not overlap each other. A separate rear cuff member 38C does overlap these arms 32C, 34C. The rear cuff member may be made of a material that is more flexible than the material of the arms 32C, 34C, and it is pivotably secured to both of the projecting arms 32C, 34C via bolts, rivets, pins, or other connectors to form two rear pivot points 36C (See FIG. 15). The rear cuff 38C provides a bridge between the two pivot legs 22C, 24C, and it allows some flexibility of lateral movement of the leg.

Figure 16:
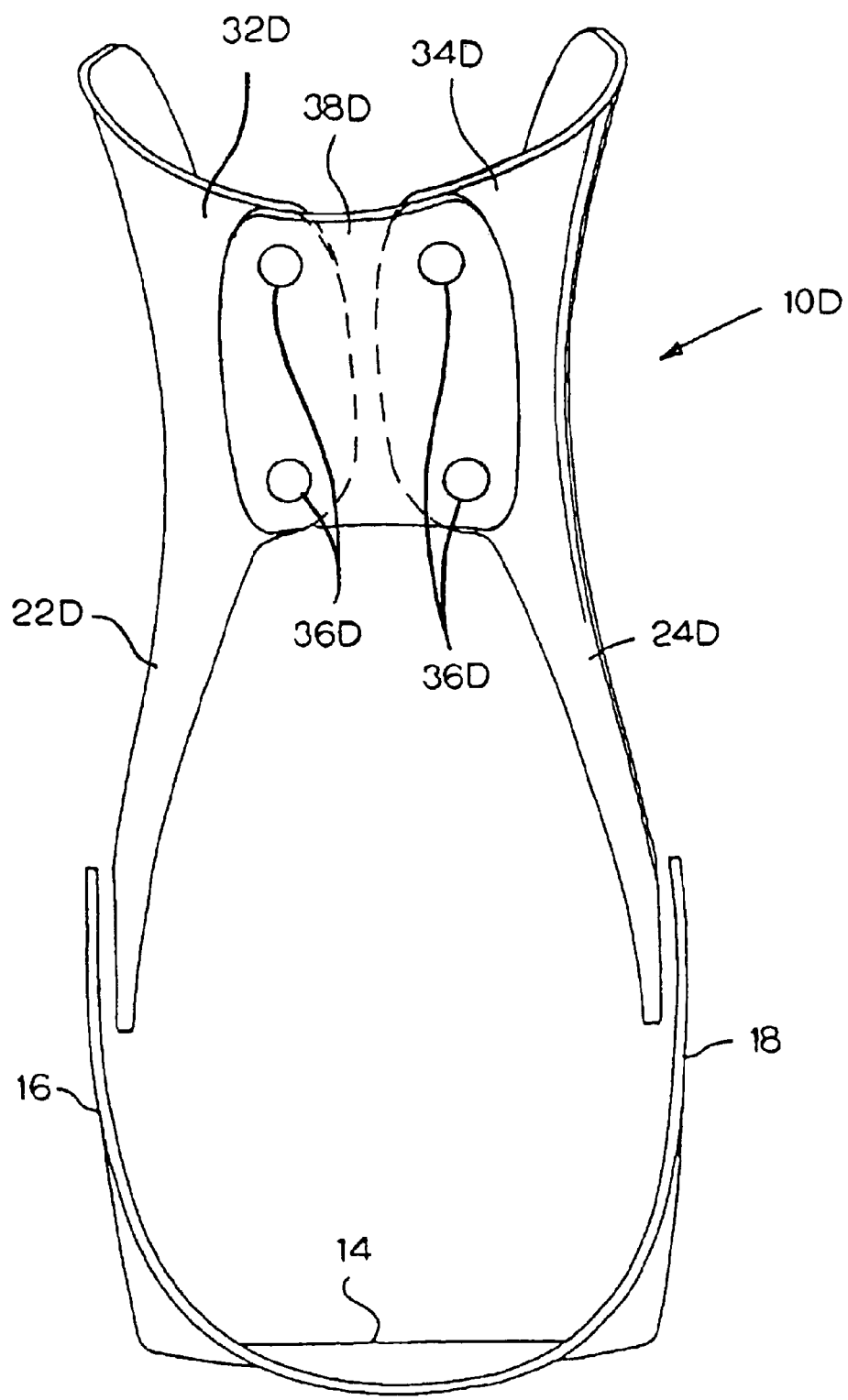
FIG. 16 is a rear view of another embodiment of an ankle brace made in accordance with the present invention, with a separate flexible rear cuff.

FIG. 16 depicts another embodiment of an ankle brace 10D, made in accordance with the present invention. This embodiment is similar to the previous embodiment 10C in that the left and right rearwardly projecting arms 32D, 34D do not overlap each other, and a separate rear cuff member 38D does overlap these arms 32D, 34D and it is secured to both of the projecting arms 32D, 34D via bolts, rivets, pins, or other connectors 36D. In this embodiment 10D, the rear cuff member 38D is preferably made from a more flexible material than the pivot legs 22D, 24D, and it is this flexibility of the material of the rear cuff 38D that allows more lateral movement of the leg than would otherwise be available if the cuff had the same flexibility as the rest of the brace.

Figure 24:
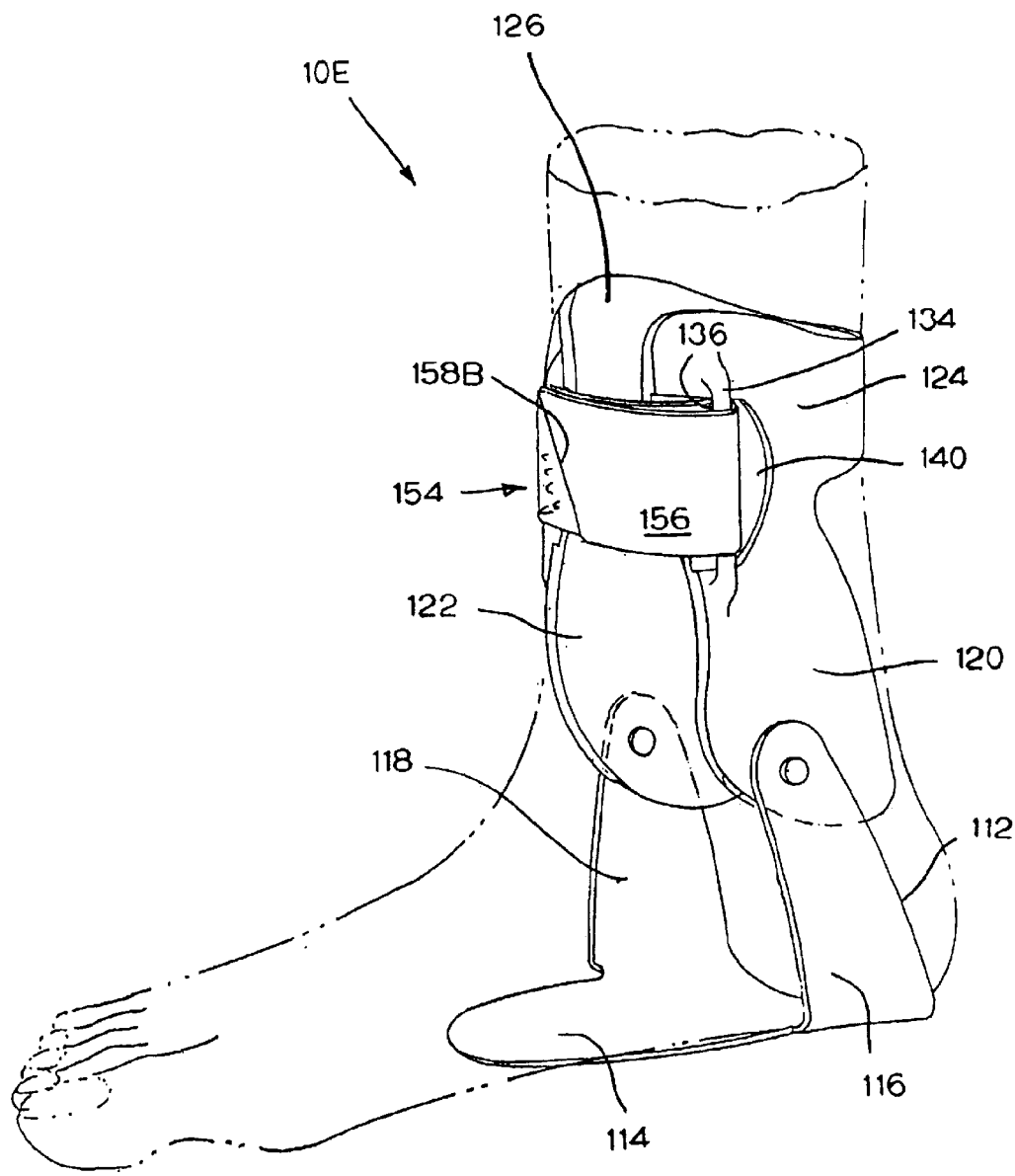
FIG. 24 is a perspective view of either of the ankle braces of FIG. 17 or 22, with the closure strap in place.
Figure 26:
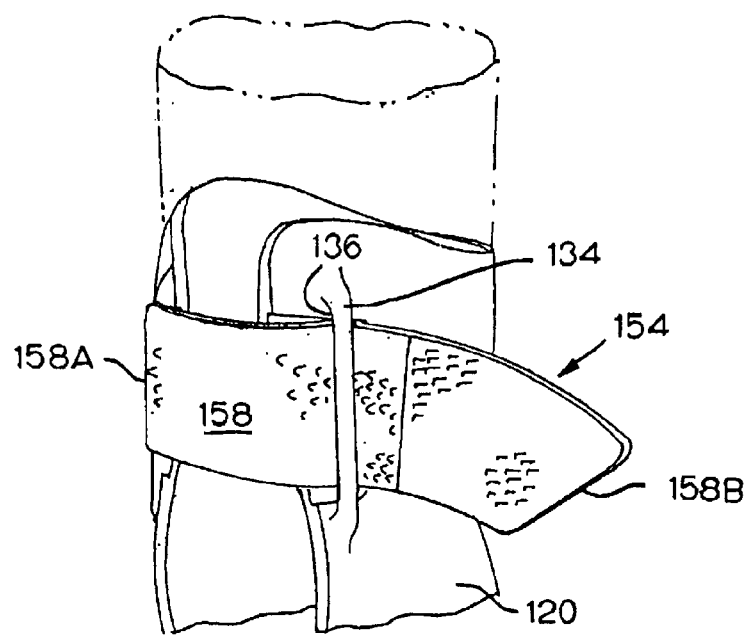
FIG. 26 is the same view as FIG. 25, except that the closure strap has been fed through the slot extension of the left pivot leg in preparation for tightening the strap onto itself.
Figure 25:
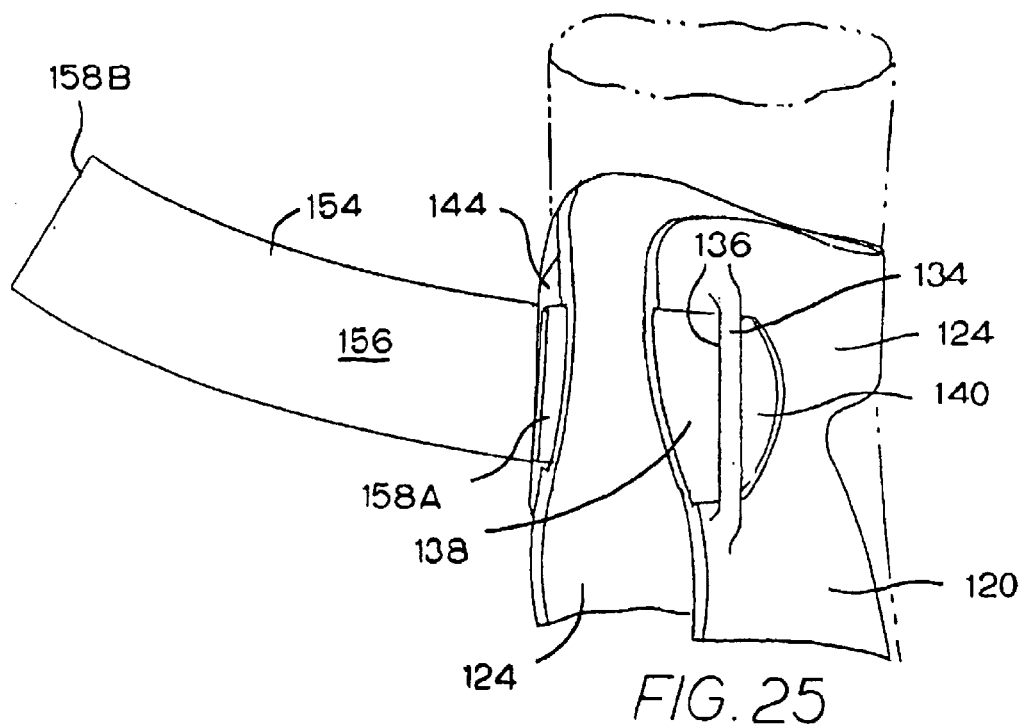
FIG. 25 is a broken-away perspective view of the ankle brace of FIG. 24 before the strap is fed through the slot extension of the left pivot leg.

FIGS. 17–21, 28, and 28A show another embodiment of an ankle brace 10E made in accordance with the present invention. FIGS. 22, 23, 27, and 29 show still another embodiment 10F. FIGS. 24–26 show a strap being mounted on either of the embodiments 10E or 10F.

FIGS. 17–21 show an ankle brace 10E made in accordance with the present invention, with the closure strap removed for clarity. The ankle brace 10E includes a substantially U-shaped heel stirrup 112 with a bottom portion 114 and left and right upright portions 116, 118, which project upwardly and are pivotally connected to left and right pivot legs 120, 122, respectively. The left and right pivot legs 120, 122 have left and right arms 124, 126, which are joined together to form a rear cuff 128. In this embodiment, the rear cuff 128 is a single, continuous piece and does not provide the flexibility of other embodiments. (In the other embodiment 10F, shown in FIG. 22, the rear cuff is formed of two pieces which are connected together at a pivot 130 as in the case of the first embodiment 10 shown in FIG. 1)

Figure 17:
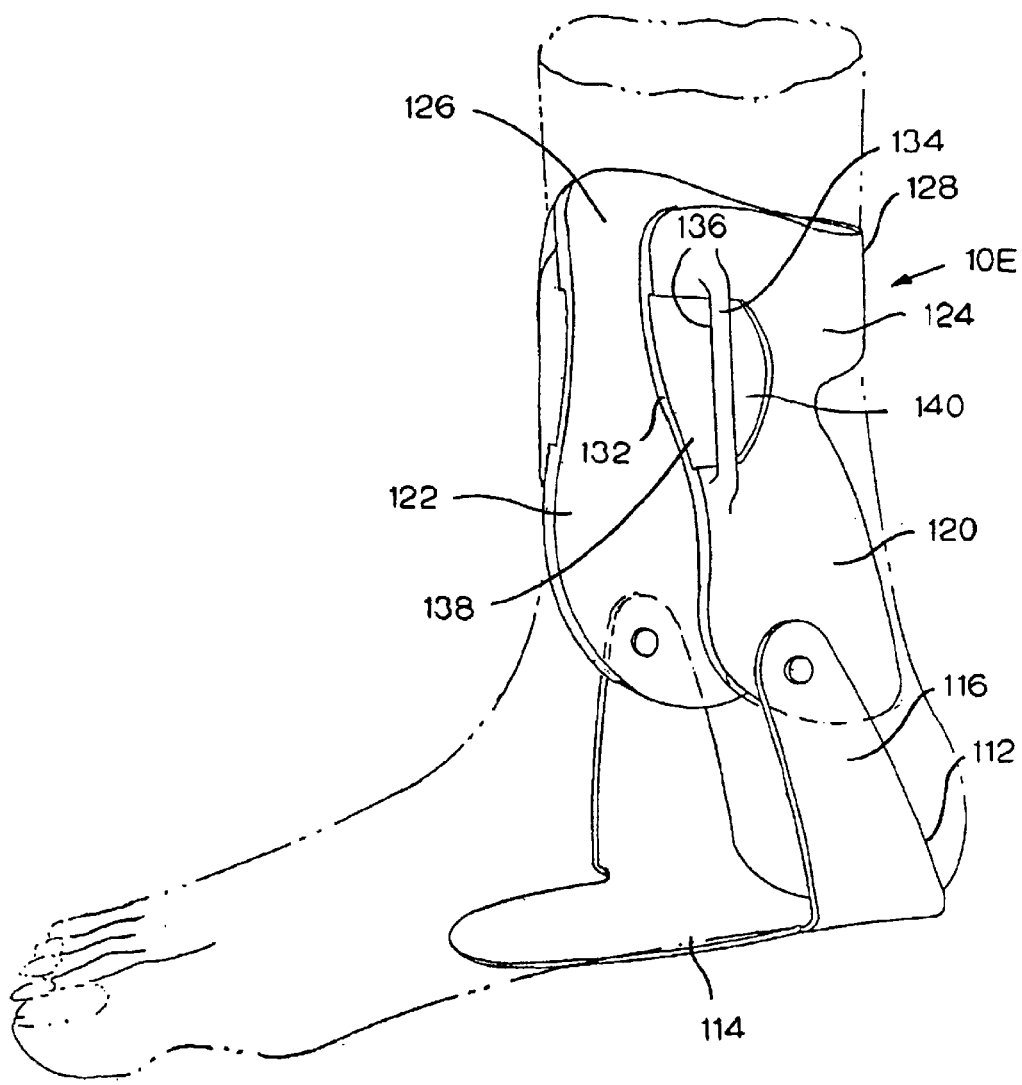
FIG. 17 is a perspective view of another embodiment of an ankle brace made in accordance with the present invention, with the closure strap removed.
Figure 20:
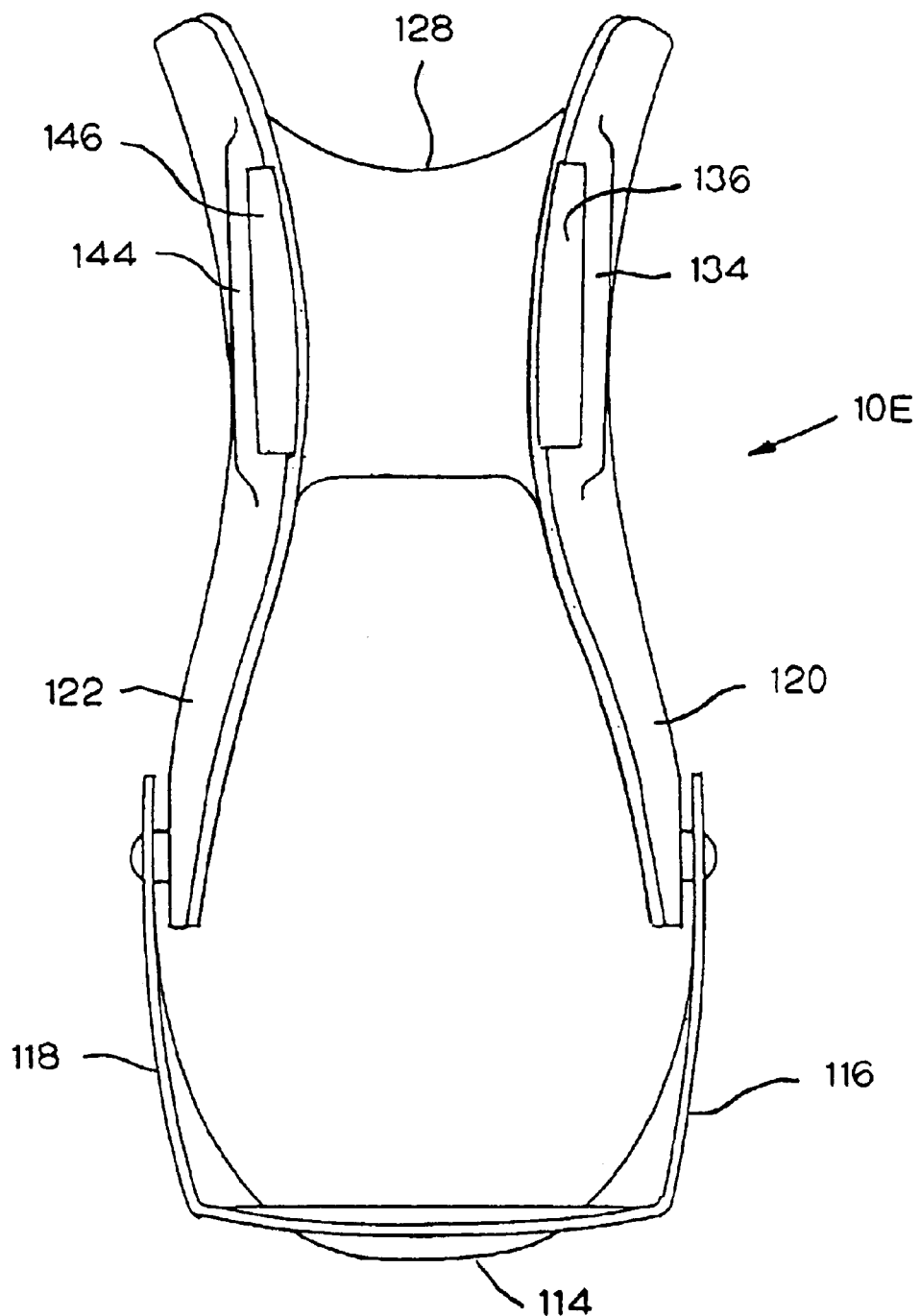
FIG. 20 is a front view of the ankle brace of FIG. 17.
Figure 21:
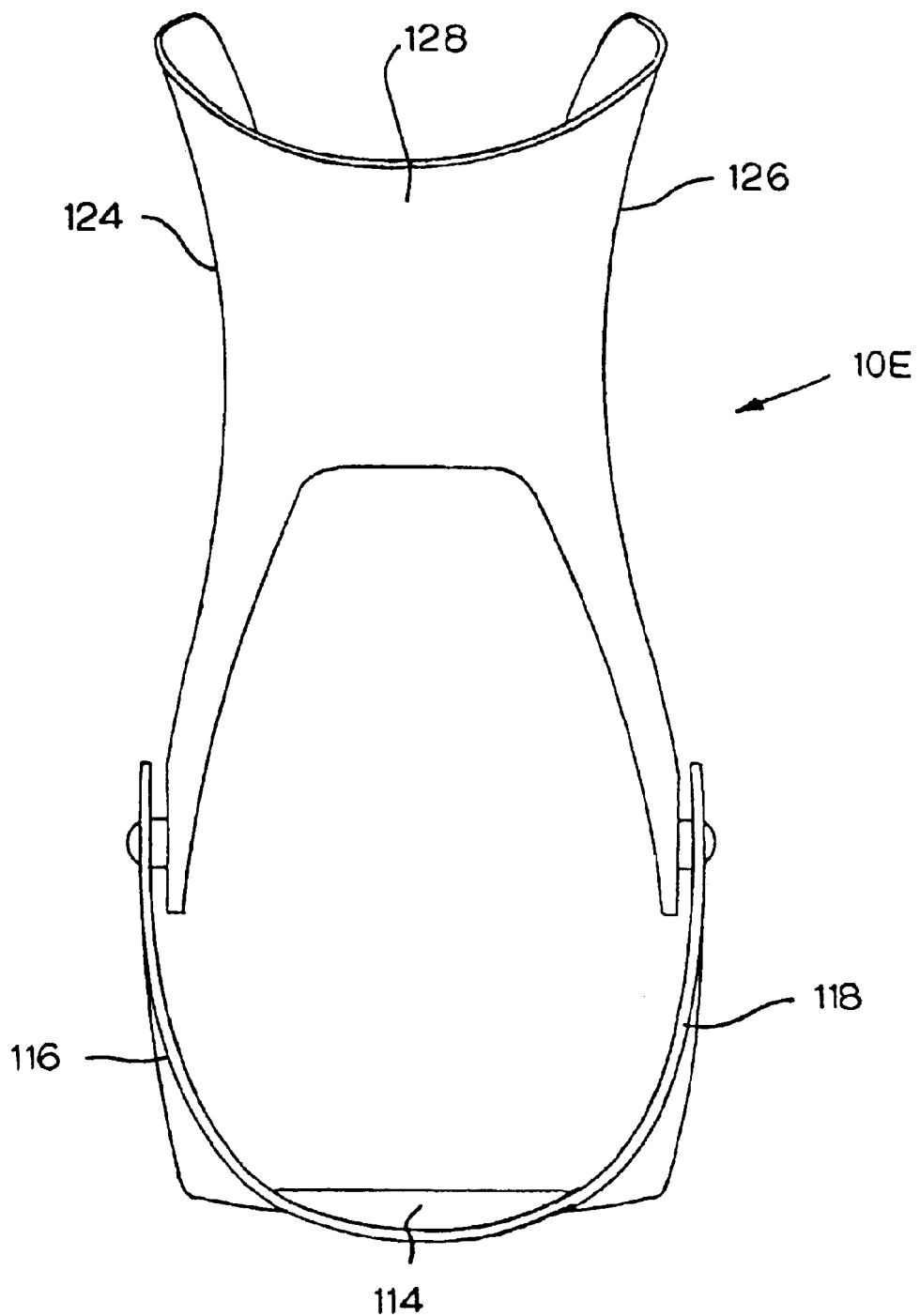
FIG. 21 is a back view of the ankle brace of FIG. 17.
Figure 22:
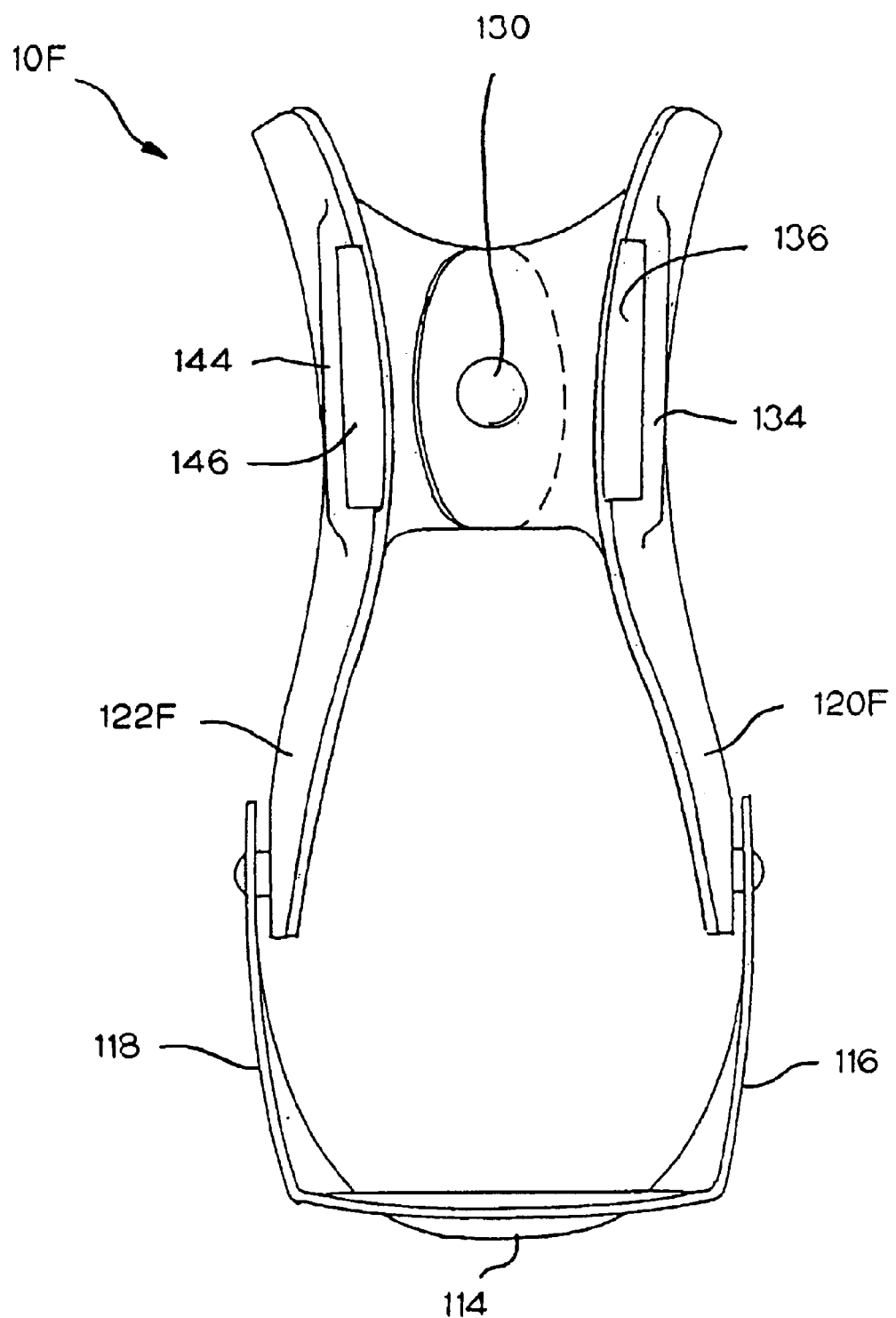
FIG. 22 is a front view, similar to FIG. 20, of another embodiment of an ankle brace made in accordance with the present invention.
Figure 23:
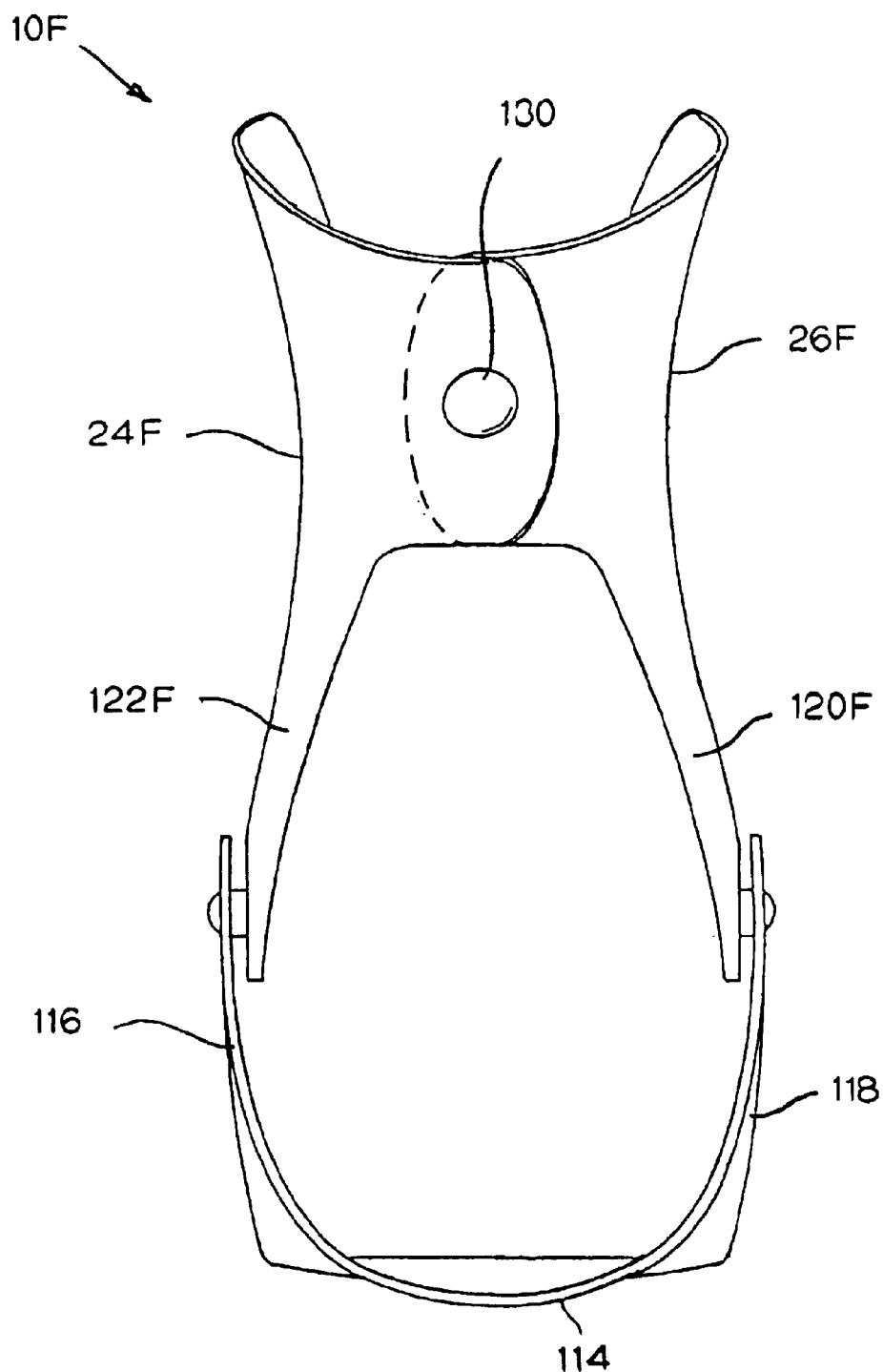
FIG. 23 is a back view of the ankle brace of FIG. 22.

The two arms 124, 126 are essentially mirror images of each other, and the cuff 128 is symmetrical along an imaginary axis, forming a generally horseshoe-shaped profile which wraps around the back of the wearer's leg as shown in FIG. 17.

Near the front edge 132 of the left arm 124 is a U-shaped, forwardly-projecting, generally vertical post 134, which is connected at its top and bottom ends to the left arm 124. The central portion of the post 134 is outwardly spaced from the outer surface of the left leg 120, forming a vertical slot 136 between the post 134 and the outer surface of the leg 120, best shown in FIG. 20. A similar post 144 is located in the same position near the front edge 142 of the right leg 122, defining a similar slotted opening 146. In this preferred embodiment 10E, the posts 134, 144 are integrally molded with the legs 120, 122. However, the ends of the posts 134, 144 may be secured to the legs 120, 122 by other substantially rigid means, such as bolting, riveting, and so forth.

The outer surface of the legs 120, 122 preferably is recessed in the area of the posts 134, 144 to help facilitate the passage of a strap through the slots 136, 146. The recessed portions of the legs 120, 122 forward of the posts 134, 144 are referred to as anterior strips 138, 148, and the recessed portions of the legs 120, 122 to the rear of the posts 134, 144 are referred to as posterior strips 140, 150. A narrow, vertical strip of hook Velcro 152 (See FIG. 19) is secured, by any suitable means such as gluing, to the anterior strip 148 of the right leg 122.

A closure strap 154 is shown in FIGS. 24–29. The strap 154 has first and second ends 158A and 158B, and first and second surfaces 156, 158. The first surface 156 preferably is a smooth surface, at least for the portion that is in contact with the wearer's leg. The second surface 158 has loop Velcro beginning at the first end 158A and extending for approximately two-thirds of the length of the strap 154. The remainder of the strap 154 is a hook Velcro, extending all the way to the second end 158B of the strap 154. The width and thickness of the closure strap 154 is such that it can fit through the slots 136, 146 on the arms 126, 124 respectively. In this preferred embodiment, the strap is approximately two inches wide and $\frac{1}{16}$-inch thick.

To use the ankle brace 10E (See FIGS. 24,25, and 26), the first end 158A of the strap 154 is fed through the slot 146 on the right leg 122 of the brace 10E such that the loop Velcro on the Velcro side 158 of the strap 154 engages with the hook Velcro strip 152 on the anterior strip of the right leg 124. The strap 154 is then bent around the post 144 on the right leg 122 and is extended across the front of the brace 10E, until the second end 158B of the strap 154 is fed through the slot 136 on the left leg 120, going first along the anterior strip 138, then through the slot 136, and then out past the posterior strip 140, as shown in FIG. 26. The smooth, fabric-like first side 156 of the strap 154 faces the wearer's leg. The user then folds the strap 154 over the post 134 on the left leg 120, and pulls the strap 154 tightly back onto itself so that the hook Velcro on the second side 158 adjacent the second end 158B of the strap 154 engages the loop Velcro on the remainder of the second side 158 of the strap 154. The brace 10E may be tightened or loosened by pulling more or less tightly on the second end 158B of the strap 154 after the strap 154 has been fed through the slot 136 and around the post 134.

Figure 28A:
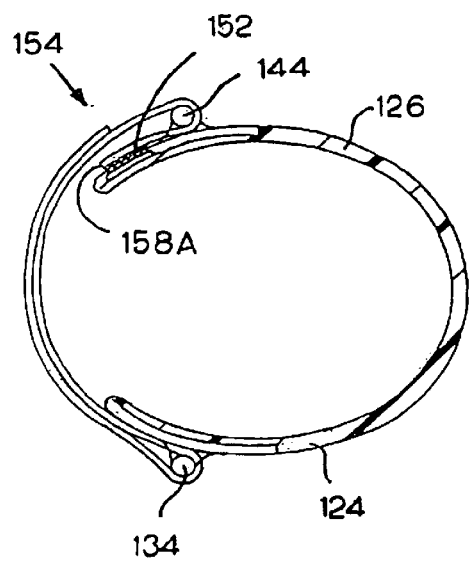
FIG. 28A is a view identical to that of FIG. 28 except that it shows the closure strap adjusted for use with a larger ankle.
Figure 29:
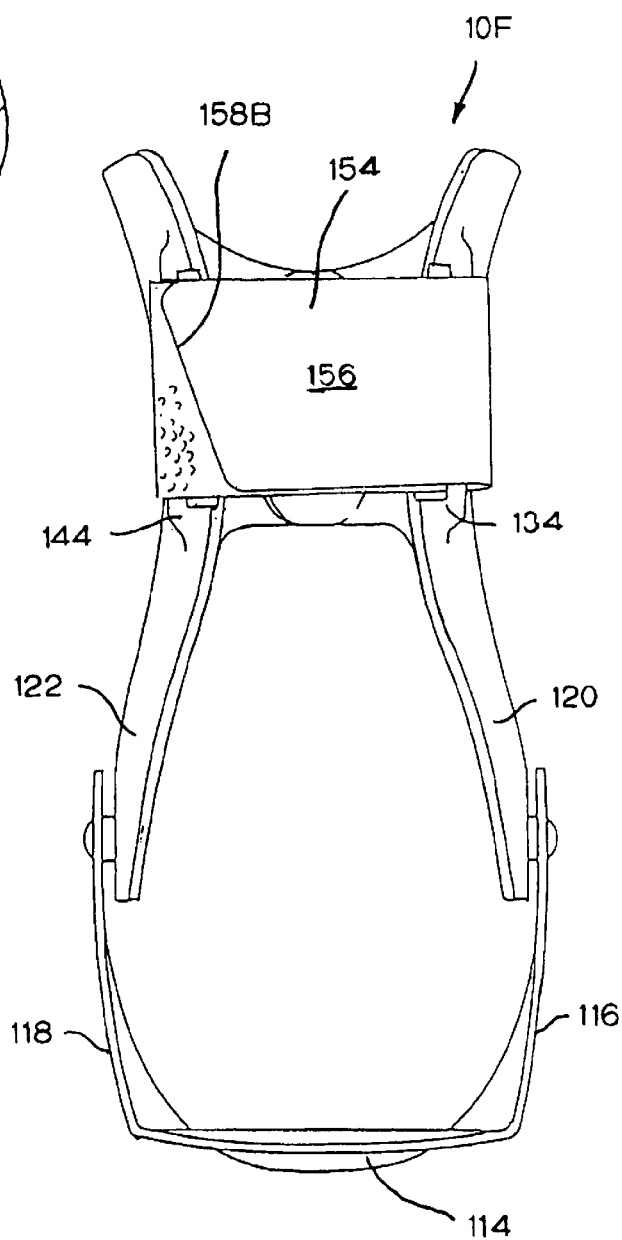
FIG. 29 is a front view of the brace of FIG. 27.

FIG. 28 shows one possible location of the strap 154, with a substantial portion of the first end 158A extending beyond the hook Velcro narrow strip 152 on the right leg 122. This would be for a person having a relatively small diameter ankle. FIG. 28A shows another possible location of the same strap 154, for use with a larger ankle. In this case, the end 158A does not extend beyond the Velcro strip 152. The connection point between the strap 514 and the strip 152 may be adjusted to effectively lengthen or shorten the strap 154.

Since the posts 134, 144 are fixed securely at both ends to the body of the ankle brace 10E and are preferably made of the same or similar material to the rest of the brace, they provide substantial rigidity at both ends of the strap 154, which helps provide a secure fit between the person's leg and the ankle brace 10E.

The strap 154 is fed through the slots and around the posts 134, 144 of the other ankle brace 10F in the same manner as in the ankle brace 10E. The only difference is that the rear cuff of the second brace 10F includes a pivot 130.

Figure 30:
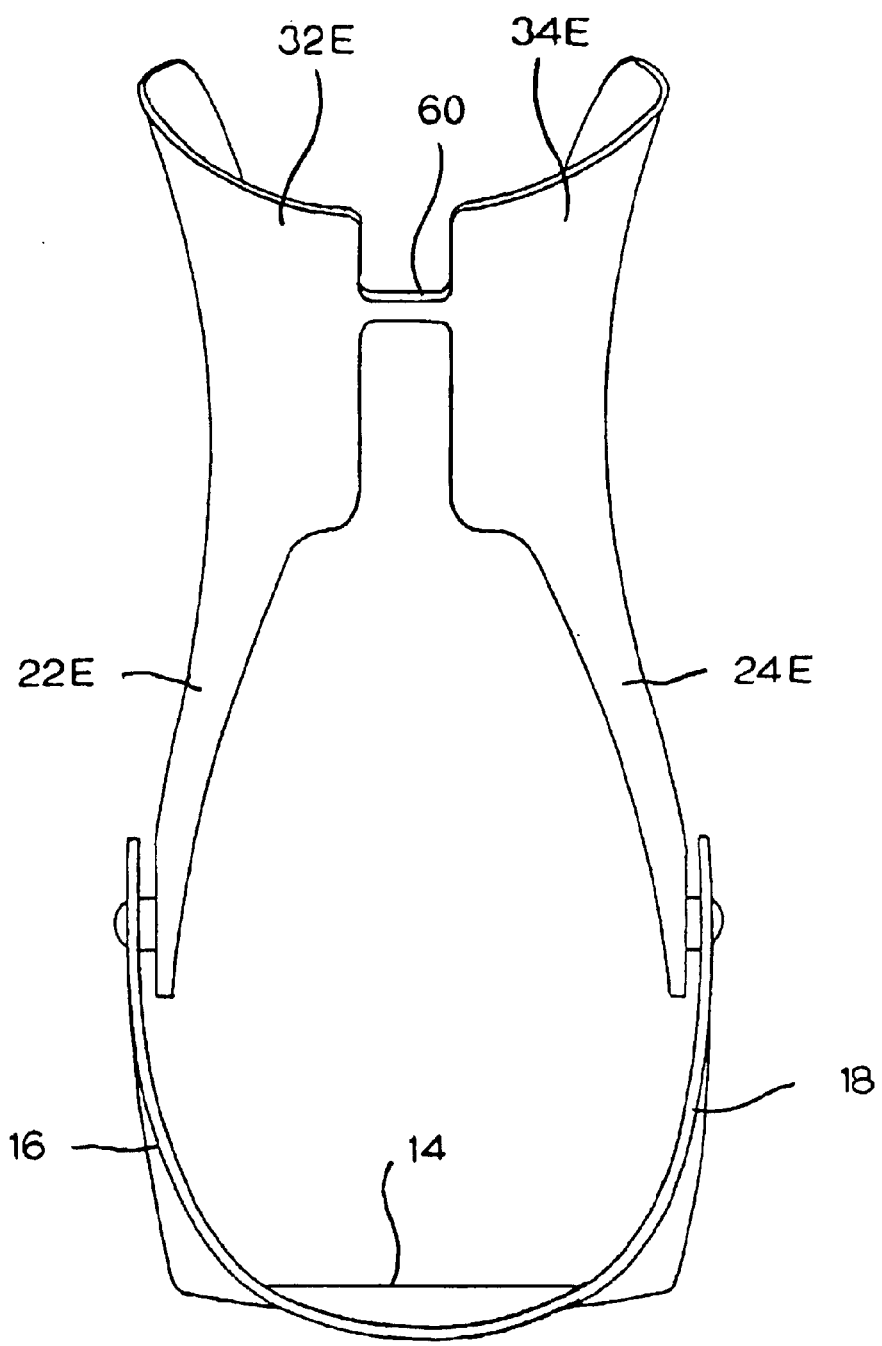
FIG. 30 is a rear view of another embodiment of a brace made in accordance with the present invention.

FIG. 30 shows another alternate embodiment of a brace made in accordance with the present invention. In this case, the legs 22E and 24E are pivotably connected to the heel stirrup as in previous embodiments, and arms 32E, 34E project rearwardly from their respective legs and join to form a flexible rear cuff. In this embodiment, the arms 32E, 34E and the legs 22E, 24E are all made as a single piece. The height of a central portion of the rear cuff has been substantially reduced to form a flexible web 60, which provides the desired structural support and flexibility to the brace.

It will be obvious to those skilled in the art that modifications may be made to the preferred embodiments described herein without departing from the scope of the present invention.

What is claimed is:

1. An ankle brace, comprising:

a substantially U-shaped heel stirrup, including a bottom portion adapted to extend under a wearer's foot and left and right upright portions adapted to extend upwardly along the left and right sides of a wearer's foot;

left and right pivot legs pivotably attached to said left and right upright portions at left and right pivot points, respectively;

left and right arms projecting rearwardly from said left and right pivot legs, respectively, wherein said left and right arms are joined together to form a rear cuff;

a first outwardly-projecting U-shaped post having top and bottom ends secured to said left arm and defining a first slot between said first post and said left arm;

a second outwardly-projecting U-shaped post having top and bottom ends secured to said right arm and defining a second slot between said second post and said right arm, said second post extending generally parallel to said first post;

a first fastener located on the outer surface of one of said arms forward of its respective post; and, a closure strap having first and second ends and first and second surfaces, said first end having a second fastener which cooperates with said first fastener to secure said first end of said strap to said one arm, and said strap further including a securing means to secure the second end of said strap to an intermediate portion of said strap, wherein said strap is fed through said first slot and through said second slot, and said second end of said strap folds back over and is secured onto itself at said intermediate portion.

2. An ankle brace as recited in claim 1, wherein said first fastener is the hook side of a hook-and-loop type fastener, said second fastener is the loop side of a hook-and-loop type fastener, and said securing means is the hook side of a hook-and-loop type fastener.

3. An ankle brace as recited in claim 1, wherein said rear cuff is flexible.

4. An ankle brace, comprising:

a U-shaped heel stirrup, including a base and first and second uprights projecting upwardly from the base, wherein the base and uprights are formed as a unitary piece;

first and second pivot legs pivotably attached to said first and second uprights, respectively;

a flexible rear cuff extending rearwardly from and attached to the upper portion of each of said pivot legs;

a first outwardly-projecting U-shaped post secured to said first pivot leg and defining a slot between said first post and said first pivot leg;

a second outwardly-projecting U-shaped post secured to said second pivot leg and defining a slot between said second post and said second pivot leg, said second post lying generally parallel to said first post;

a first fastening means located on the outer surface of said first pivot leg forward of said first post; and, a closure strap having first and second ends and first and second surfaces, said first end having a second fastening means which cooperates with said first fastening means to secure said first end of said strap to said first pivot leg, and said second end of said strap having third fastening means to secure said strap to itself, wherein said strap is fed through said first slot and through said second slot, and said second end folds back over onto itself.

* * * * *